US012678523B2

(12) United States Patent
Baarman

(10) Patent No.: US 12,678,523 B2
(45) Date of Patent: Jul. 14, 2026

(54) SYSTEM AND METHOD OF DISINFECTION

(71) Applicant: UV Partners, Inc., Grand Haven, MI (US)

(72) Inventor: David W Baarman, Fennville, MI (US)

(73) Assignee: UV Partners, Inc., Holland, MI (US)

( * ) Notice: Subject to any disclaimer, the term of this patent is extended or adjusted under 35 U.S.C. 154(b) by 1022 days.

(21) Appl. No.: 17/368,914

(22) Filed: Jul. 7, 2021

(65) Prior Publication Data

US 2023/0011728 A1      Jan. 12, 2023

(51) Int. Cl.
    *A61L 2/10*          (2026.01)

(52) U.S. Cl.
    CPC ............. *A61L 2/10* (2013.01); *A61L 2202/11* (2013.01); *A61L 2202/122* (2013.01); *A61L 2202/14* (2013.01)

(58) Field of Classification Search
    CPC ........................................................ A61L 2/10
    See application file for complete search history.

(56) References Cited

U.S. PATENT DOCUMENTS

| | | | |
|---|---|---|---|
| 5,379,201 A | 1/1995 | Friedman | |
| 6,278,122 B1 | 8/2001 | Gagnon | |
| 8,114,346 B2 | 2/2012 | Hyde et al. | |
| 9,623,138 B2 | 4/2017 | Pagan et al. | |
| 2002/0155027 A1 | 10/2002 | Gutman | |
| 2004/0190281 A1 | 9/2004 | Williams et al. | |
| 2006/0188389 A1 | 8/2006 | Levy | |
| 2008/0310996 A1* | 12/2008 | Kim ......................... | A61L 9/20 |
| | | | 422/186.3 |

| | | | |
|---|---|---|---|
| 2009/0218512 A1 | 9/2009 | Ranta et al. | |
| 2012/0282135 A1 | 11/2012 | Trapani | |
| 2013/0045132 A1 | 2/2013 | Tumanov | |
| 2013/0062534 A1 | 3/2013 | Cole | |
| 2014/0183377 A1 | 7/2014 | Bettles et al. | |
| 2016/0000953 A1* | 1/2016 | Bettles ...................... | A61L 2/10 |
| | | | 250/455.11 |
| 2017/0290934 A1* | 10/2017 | Dobrinsky ......... | G02B 19/0095 |
| 2021/0330081 A1* | 10/2021 | McMillin .................. | A61L 2/10 |
| 2023/0031285 A1* | 2/2023 | Goza ...................... | G06F 1/1643 |
| 2023/0248862 A1* | 8/2023 | Benner ...................... | A61L 2/10 |
| | | | 422/24 |

FOREIGN PATENT DOCUMENTS

| | | |
|---|---|---|
| GB | 2 375 504 | 11/2002 |
| GB | 2 421 217 | 6/2006 |
| WO | 2008/096123 | 8/2008 |
| WO | 2015/184428 | 12/2015 |
| WO | 2019/190967 | 10/2019 |

OTHER PUBLICATIONS

Renesas, "Introduction of Proximity Sensing", available at https://www.renesas.com/us/en/document/apn/an1436-introduction-proximity-sensing, Mar. 26, 2009, pp. 1-10.
International Search Report and the Written Opinion of the International Searching Authority for International Application No. PCT/US2022/034429 mailed Oct. 31, 2022.

\* cited by examiner

*Primary Examiner* — Donald R Spamer
*Assistant Examiner* — Kayla Rose Sarantakos
(74) *Attorney, Agent, or Firm* — Warner Norcross + Judd LLP

(57)        ABSTRACT

A system and method for a UV disinfection device configured to be disposed to direct UV energy through an exit interface toward a target surface of a device. The UV disinfection device may be configured for low-profile distribution of UV energy toward the target surface.

31 Claims, 30 Drawing Sheets

| ADJUSTMENT SCREW | MIRROR GAP | MIRROR ANGLE |
|---|---|---|
| | mm | DEGS |
| −14 | 1.967 | 3.28 |
| −13 | 1.9 | 3.05 |
| −12 | 1.83 | 2.82 |
| −11 | 1.761 | 2.58 |
| −10 | 1.693 | 2.35 |
| −9 | 1.623 | 2.11 |
| −8 | 1.553 | 1.88 |
| −7 | 1.485 | 1.65 |
| −6 | 1.416 | 1.41 |
| −5 | 1.346 | 1.18 |
| −4 | 1.279 | 0.94 |
| −3 | 1.208 | 0.71 |
| −2 | 1.138 | 0.47 |
| −1 | 1.07 | 0.24 |
| 0 | 1 | 0.00 |
| 1 | 0.93 | 0.24 |
| 2 | 0.862 | 0.47 |
| 3 | 0.792 | 0.71 |
| 4 | 0.722 | 0.95 |
| 5 | 0.653 | 1.19 |
| 6 | 0.583 | 1.43 |
| 7 | 0.513 | 1.67 |
| 8 | 0.444 | 1.90 |
| 9 | 0.374 | 2.15 |
| 10 | 0.304 | 2.39 |
| 11 | 0.235 | 2.63 |
| 12 | 0.165 | 2.87 |
| 13 | 0.095 | 3.11 |
| 14 | 0.026 | 3.35 |

| TOP DUT | | | | | |
|---|---|---|---|---|---|
| 134.2 | 285.1 | 310.6 | 279.4 | 264.3 | 124.1 |
| 85.8 | 148 | 156.5 | 165.7 | 143.6 | 81.7 |
| 58.6 | 94.8 | 110.6 | 106.8 | 89.4 | 56.6 |
| 42.95 | 63.2 | 82.2 | 72.9 | 60.2 | 42.09 |
| 33.51 | 46.33 | 48.24 | 53.7 | 45.69 | 32.06 |
| 35.83 | 37.02 | 39.279 | 43.899 | 37.5 | 35.52 |
| 34.86 | 37.03 | 37.515 | 36.605 | 36.66 | 35.58 |
| 28.614 | 36.42 | 35.07 | 31.76 | 33.56 | 29.534 |
| 23.021 | 26.23 | 30.92 | 28.35 | 28.01 | 22.911 |
| 18.598 | 21.16 | 24.34 | 23.42 | 23.34 | 18.318 |
| BOTTOM REFLECTOR | | | | | |

*134"*
*+/- 50μm*

*131"*
*+/- 5μm*

*133"*

STACK:

| | |
|---|---|
| *DIE, 131"* | *+/- .0002"* |
| *134" PLACEMENT* | *+/- .002"* |
| *PCBA, 133"* | *+/- .005"* |
| *TOTAL* | *+/- .0072* |

*TOTAL = 0.0144"*
*1μm = 0.039"*

*140"*

*EDGE CONTACT*
*SPACE KEEP-OUT*

Z AXIS
PCBA +/- .005"
CHIP  +/- .001"
SOLDER +/- .002"
HEATSINK LOCATION +/- .005"

EXAMPLE LIFE CYCLE CALCULATIONS

| Cycles per day | Days per year | Dose Time | Cycles per year | Minutes of time per year | Hours | LED Life L70 | Years of use |
|---|---|---|---|---|---|---|---|
| 20 | 365 | 3 | 7,300 | 21,900 | 365 | 5,000 | 14 |
| 100 | 365 | 3 | 36,500 | 109,500 | 1,825 | 5,000 | 3 |
| 200 | 365 | 3 | 73,000 | 219,000 | 3,650 | 5,000 | 1 |
| 300 | 365 | 3 | 109,500 | 328,500 | 5,475 | 5,000 | 1 |
| 400 | 365 | 3 | 146,000 | 438,000 | 7,300 | 5,000 | 1 |
| 20 | 365 | 3 | 7,300 | 21,900 | 365 | 7,500 | 21 |
| 100 | 365 | 3 | 36,500 | 109,500 | 1,825 | 7,500 | 4 |
| 200 | 365 | 3 | 73,000 | 219,000 | 3,650 | 7,500 | 2 |
| 300 | 365 | 3 | 109,500 | 328,500 | 5,475 | 7,500 | 1 |
| 400 | 365 | 3 | 146,000 | 438,000 | 7,300 | 7,500 | 1 |
| 20 | 365 | 3 | 7,300 | 21,900 | 365 | 10,000 | 27 |
| 100 | 365 | 3 | 36,500 | 109,500 | 1,825 | 10,000 | 5 |
| 200 | 365 | 3 | 73,000 | 219,000 | 3,650 | 10,000 | 3 |
| 300 | 365 | 3 | 109,500 | 328,500 | 5,475 | 10,000 | 2 |
| 400 | 365 | 3 | 146,000 | 438,000 | 7,300 | 10,000 | 1 |

*Calculations relate to all LEDs being on for each cycle. Partial activation of LEDs for zones may improve life*
*L70 assumes 70% of output at end of life. The system can compensate with dosage time*
*Example replacement Schedule:*

2   Year - Replacement?

| McDonalds Locations | 25000000 | customers per day |
|---|---|---|
| | 37000 | |
| | 675.68 | customer per day per store average |
| | 50% | drive thru business |
| | 338 | internal customers |
| | 4 | POS systems |
| | 84.46 | customers per POS system |

DEVICE LIFETIME (FORWARD CURRENT = 250mA, Tj<35°C)

| PARAMETER | SYMBOL | UNIT | MIN. | TYP. | MAX. |
|---|---|---|---|---|---|
| 70% POWER LIFETIME | L70 | HOURS | 1500# | 3000# | 4000# |
| 50% POWER LIFETIME | L50 | HOURS | 2500# | 5000# | 6000# |

*Fig. 39*

SYSTEM AND METHOD OF DISINFECTION

FIELD OF INVENTION

The present disclosure relates generally to disinfection systems, and more particularly to a disinfection system for a device, such as a touch screen device or user interface device.

BACKGROUND

Conventional disinfection solutions range from shining a basic UV light on the surface to providing antimicrobials in materials. Conventional systems may have raised fixtures that limit intensity of UV light in order to prevent exposing the user to significant amounts of UV light. These raised fixtures can enable greater exposure to a user and therefore only limited disinfection is considered possible while avoiding significant consumer exposure. UV LEDs have been used in conventional systems to shine UV energy across the surface for disinfection. However, in this conventional configuration, the intensity used for disinfection is limited to NIOSH limits and is restricted in angle of application in order to prevent significant user exposure. Although this configuration may be considered helpful for disinfecting, these limitations impact the speed of disinfection unless sensors and interesting optics are utilized.

Conventional disinfection systems are not designed for ease of interaction and are often not designed for intelligent automated interaction. More specifically conventional disinfection systems do not reduce or minimize the angle of exposure optically, leading to greater exposure potential and longer disinfection cycles.

Conventional disinfection technologies lack in an understanding of UV impact to devices. For instance, a previous directive of more UV intensity being better may have negative ramifications to the NIOSH limits, human exposure, and the destruction of materials not intended for intense UV exposure.

SUMMARY

The present disclosure in accordance with one embodiment provides a UV disinfection device including a support member operable to facilitate mounting the UV disinfection device to a surface. The UV disinfection device may include a germicidal energy source operable to generate UV energy, and a UV reflection chamber having a first reflector and an exit interface. The first reflector may be operable to receive UV energy generated by the germicidal energy source and to direct UV energy toward the exit interface, and the first reflector may be operable to direct UV energy within a UV energy region to a target surface through the exit interface. The exit interface may include a proximal portion and a distal portion relative to a first edge of the target surface, where the exit interface includes an exit interface height defined between the proximal portion and the distal portion, and where the exit interface height is significantly less than a target surface distance between the first edge of the target surface and a second edge of the target surface that is opposite the first edge of the target surface.

The foregoing and other embodiments can each optionally include one or more of the following features, alone or in combination. In particular, one embodiment includes all the following features in combination.

In one embodiment, the UV disinfection device may include a distal portion is distal from the proximal portion of the exit interface and distal from the first edge of the target surface. The distal portion and the proximal portion may define an exit interface plane through which UV energy traverses toward the target surface, and the UV energy may exit the exit interface between the proximal portion and the distal portion of the exit interface.

In one embodiment, the UV disinfection device may be configured such that the exit interface height corresponds to a distance between the proximal portion and the distal portion.

In one embodiment, the UV disinfection device may be configured such that the UV energy reflected from the first reflector is directed toward the target surface at an angle less than 90° relative to the exit interface.

In one embodiment, the UV disinfection device may be configured such that the exit interface includes a mask operable to affect a distribution of UV energy output from the exit interface.

In general, one innovative aspect of the subject matter described herein can include a UV disinfection device for disinfecting a target surface including a support member operable to facilitate mounting the UV disinfection device for disinfecting the surface. The UV disinfection device may include a germicidal energy source operable to generate UV energy, and a UV reflection chamber having a first reflector and an exit interface. The first reflector may be operable to receive UV energy generated by the germicidal energy source and to direct UV energy toward the exit interface. The exit interface may be adjacent a first edge of the target surface of the device, and the exit interface may have a height significantly less than a target surface distance between the first edge and a second edge of the target surface opposite the first edge. The first reflector may be configured to direct the UV energy through the exit interface and within a UV energy region to the target surface, where the UV energy region is defined by the target surface and an opposing boundary line that converges toward the target surface.

The foregoing and other embodiments can each optionally include one or more of the following features, alone or in combination. In particular, one embodiment includes all the following features in combination.

In one embodiment, the UV disinfection device may be configured such that the opposing boundary line converges with the target surface at a point distal from the UV disinfection device.

In one embodiment, the UV disinfection device may be configured such that a first intensity of first UV energy proximal to the first edge is greater than a second intensity of second UV energy distal from the first edge, wherein the first UV energy is directed toward the second edge, and wherein the second UV energy is directed toward the first edge.

In one embodiment, the UV disinfection device may be configured such that the UV energy output from the exit interface is substantially confined to the UV energy region, where a distance between the opposing boundary line of the UV energy region and the target surface is significantly less than the target surface distance.

In general, one innovative aspect of the subject matter described herein can include a method of operating a UV disinfection device, the method may include generating UV energy from a germicidal energy source, and reflecting the UV energy toward an exit interface of the UV disinfection device. The method may include directing UV light energy at a distribution height toward a distal edge of a target surface, the distal edge being opposite a proximal edge of the target surface that is proximal to the UV disinfection device, where the distribution height may be significantly less than a distance between the distal edge and the proximal edge of the target surface.

The foregoing and other embodiments can each optionally include one or more of the following features, alone or in combination. In particular, one embodiment includes all the following features in combination.

In one embodiment, the method may include directing UV light energy at a proximal height toward the proximal edge of the target surface, where the proximal height is less than the distribution height.

In one embodiment, the method may include providing a diffuser disposed within a UV reflection chamber and arranged to receive UV energy output from the germicidal energy source.

These and other advantages and features of the invention will be more fully understood and appreciated by reference to the description of the current embodiment and the drawings.

Before the embodiments of the invention are explained in detail, it is to be understood that the invention is not limited to the details of operation or to the details of construction and the arrangement of the components set forth in the following description or illustrated in the drawings. The invention may be implemented in various other embodiments and of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components. Any reference to claim elements as "at least one of X, Y and Z" is meant to include any one of X, Y or Z individually, and any combination of X, Y and Z, for example, X, Y, Z; X, Y; X, Z; and Y, Z.

BRIEF DESCRIPTION OF THE DRAWINGS

FIG. 39 showing a replacement schedule based on cycles and minutes of pathogen reduction cycles in accordance with one embodiment.

DESCRIPTION

Figures 1, 2:
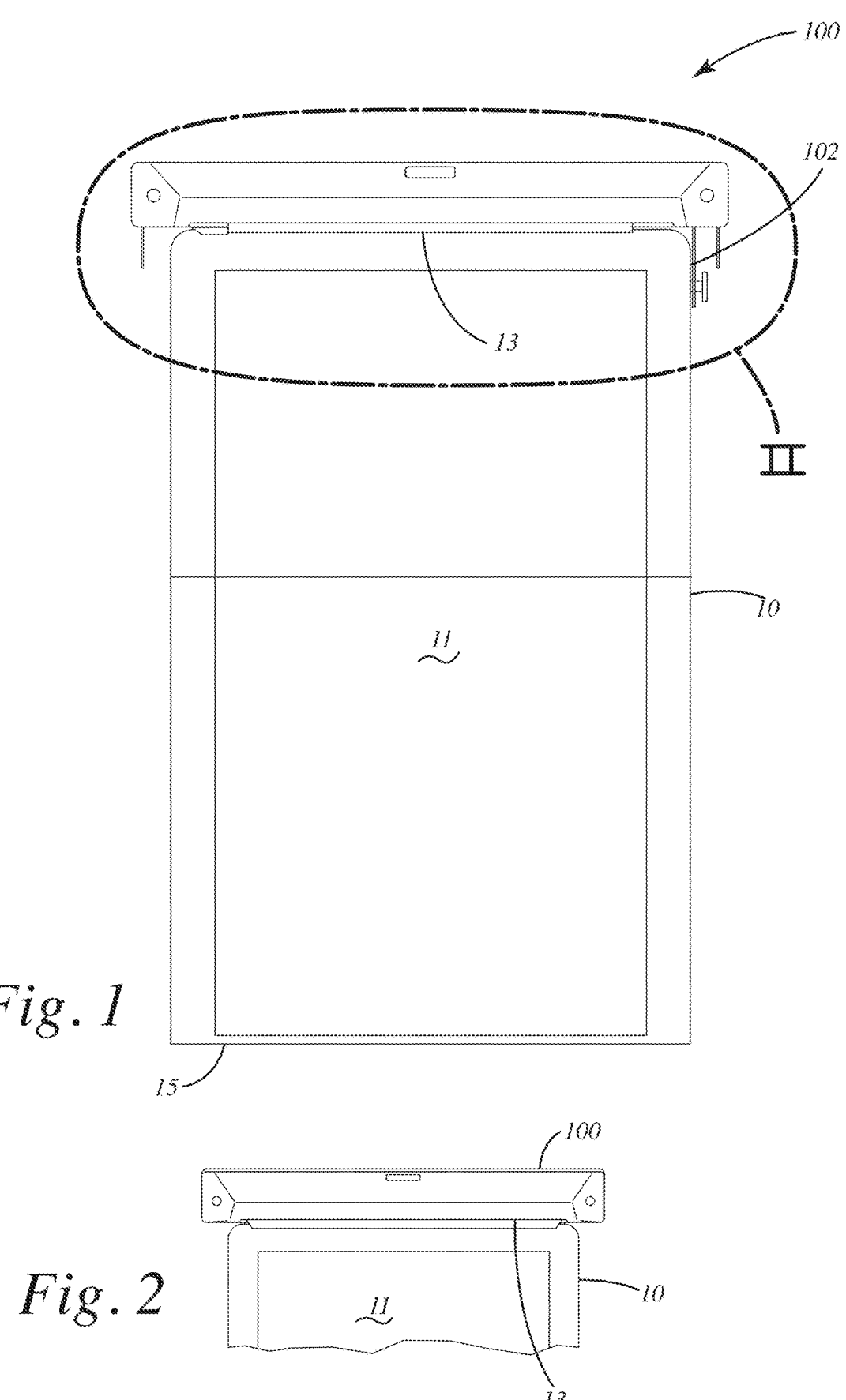
FIG. 1 shows a UV disinfection system in accordance with one embodiment.
FIG. 2 shows an enlarged view of the UV disinfection system of FIG. 1.
Figure 3:
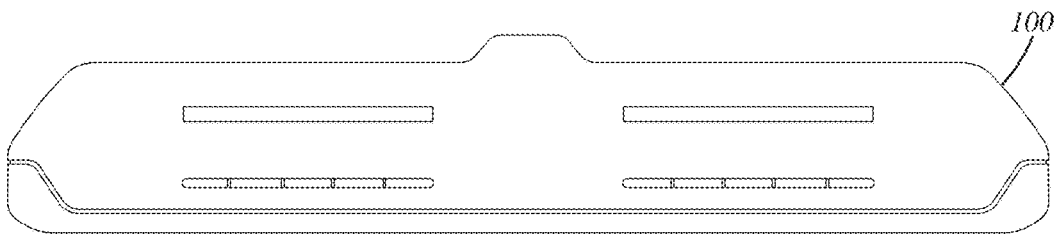
FIG. 3 shows a rear view of the UV disinfection system in accordance with one embodiment.
Figure 4:
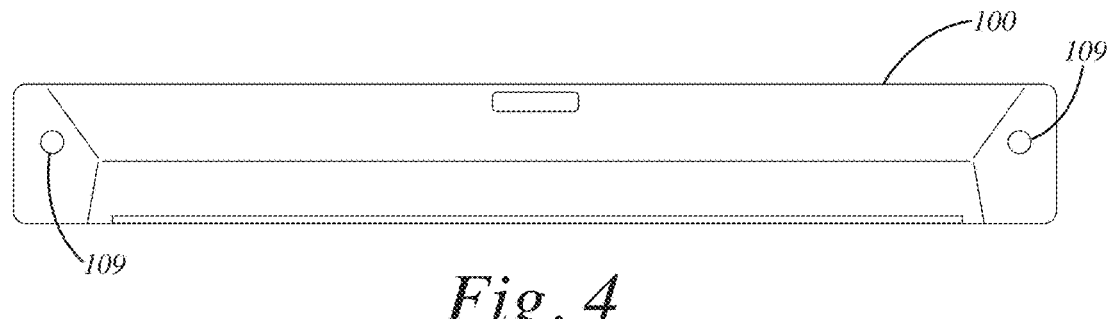
FIG. 4 shows a top view of the UV disinfection system of FIG. 3.

A system and method in accordance with one embodiment may include a UV disinfection device configured to be disposed to direct UV energy through an exit interface toward a target surface of a device. The UV disinfection device may be configured for low-profile distribution of UV energy toward the target surface. For instance, a height of the exit interface may be significantly less than a distance of the target surface over which the UV new energy is distributed from the exit interface. The height of the exit embodiment may be 2 mm or less, or 1 mm or less. A ratio of the distance relative to the height, in one embodiment, may be five or greater, 10 or greater, 20 or greater, 50 or greater, 75 or greater, or 100 or greater, or a range therein. As another example, an angle of UV energy distributed from the exit interface relative to the target surface may be less than 5°, less than 3°, less than 1°, less than 0.5°, and less than 0.25°, or a range therein. The angle of UV energy distribution from the exit interface may be adjustable in accordance with one or more embodiments described herein, depending on the application and the area of the target surface to be disinfected.

A system and method in accordance with one embodiment may provide a low cost, simple to implement disinfecting configuration that is low profile, waterproof, and non-intrusive, or a subset thereof. The disinfecting configuration may be tamper proof as it can be part of the display surface with portions of the disinfecting configuration located below the display surface.

In one embodiment, a UV disinfection device for delivering UV energy across a surface with a reduced or minimum device profile and having a low profile of energy to reduce or minimize human exposure is provided. The UV disinfection device may include a UV transmissive lens that is constructed to be waterproof. The optical system may be configured to deliver a substantially even dosage over a large surface. This disinfecting system may have an automatic interlock to enhance protection for the user from UV exposure and logs the exposure limits versus exposure. The UV disinfection device may be connected to a cloud based system that enables an ecosystem and cross statistic sharing of safety parameters.

The UV disinfection device in accordance with one embodiment may be configured to effectively deliver UV energy across a target surface or multiple target surfaces. This UV disinfection device may include a periscope-like configuration to deliver energy from below the target surface through an exit interface (e.g., a transmissive lens) and toward the target surface. The distribution of UV energy from the exit interface may include a uniform pattern. In one embodiment, the patterned UV energy is low profile having a low angle across the target surface. This low-profile in one embodiment may substantially limit a user's exposure to UV energy.

In one embodiment, because the UV sources, electronics, and optics are beneath the target surface of the target treatment area, one or more of these components may be ruggedized and waterproofed without significantly affecting an outward appearance and configuration of the target surface. For instance, in one embodiment, the only exposed area to a user is the bezel and delivery optic above the target surface. To prevent shock, handling, and water from changing or impacting the UV delivery, the UV components may be provided in a housing configured accordingly in a manner that is largely inconspicuous.

In one embodiment, the ability to control the UV delivery at a low profile enables delivery of UV dosing while the user is using the target surface (e.g., a touch surface). This mode of operation may allow the device to be ON from the start of touches to the completion of the dosage. The system may determine to disable the UV distribution to limit human exposure. In one embodiment, the system may shut off when the user is touching the target surface and begin applying UV energy again after touching has ceased.

In one embodiment, the UV disinfection device may include UV translucent materials operable to disperse the UV energy from the UV source to assist in homogenous delivery of UV energy. For instance, the optic may be in the form of a cylinder, which may simplify fabrication of the optical due to ease of manufacture for cylindrical optics. The fabrication of this optic may or may not include introduction of bubbles to assist in the delivery or dispersant of UV energy. Bubbles may be configured to have different chemical or gas entrainment to enhance the dispersal and may be tuned to the UV wavelength of the UV energy.

In one embodiment, the UV disinfection device may be enabled to treat long and short distances with various configurations. For instance, UV LEDs may be provided that are end lighting a polished optic. As another example, a side lighted optic may be provided with LEDs that may allow more than two LEDs to light the optic. A matching gel may be provided in some embodiments to provide additional power or coupling over configurations without matching gel. In one embodiment, depending on the coupling specifications, an intermediate optic may be provided that matches the LED UV delivery to the intermediate optic and then also matches that energy to a secondary optic. Matching gel may also be used on both of these surfaces for enhanced coupling.

In one embodiment, the system may utilize multiple inputs for enhanced safety and dose delivery control. The first input may be a TOF sensor that provides sensor information to the system that is indicative of whether a person is standing in front of the device (e.g., in front of a kiosk or POS system). This sensor feedback from the TOF sensor (or another presence sensor) may start the process of being aware when a touch occurs or is capable of occurring. The next is a link or sensor feedback into a touch system. That link may enable the system to start or stop the distribution of UV energy for the moment or duration of a touch and then to restart when that touch is completed. A gyro and accelerometer may be provided to assure the UV disinfection device is not under repair or being vandalized. The gyro may enable an angular limit, while the accelerometer provides another way of tracking touches. Motion sensors can be added when or in case a touch interface is not allowable or feasible.

Figures 18, 19:
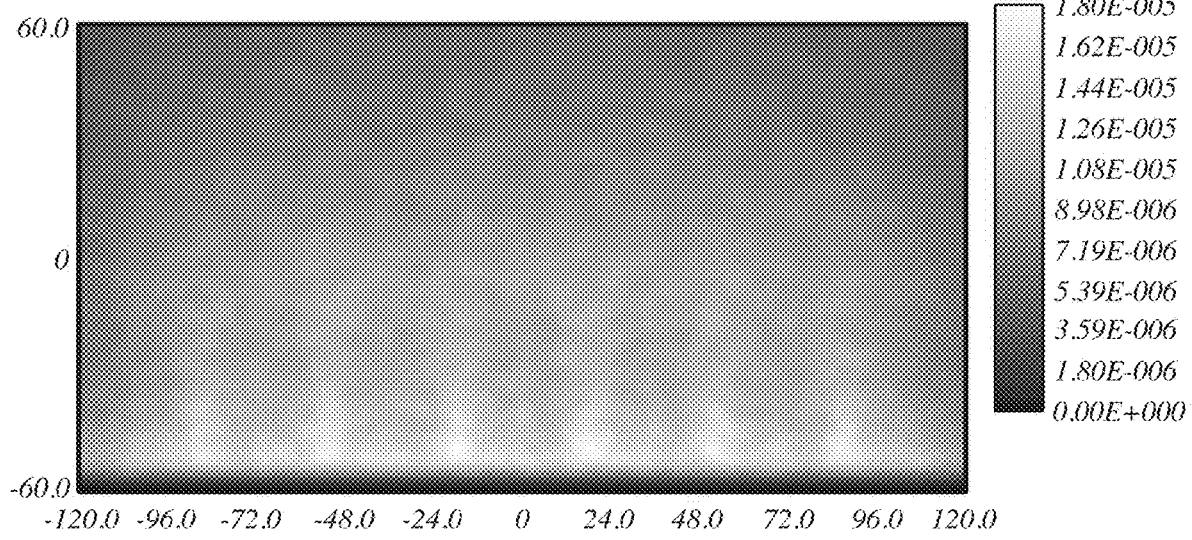
FIG. 18 shows a table of measured UV intensity for a target surface in accordance with one embodiment.
FIG. 19 shows the distribution of UV energy for a target surface in accordance with one embodiment.

In one embodiment, the delivery pattern of energy from top to bottom may be similar to the pattern depicted in FIG. 18. The target in the illustrated embodiment is 10 uW/cm2 energy over the whole of the target surface. The chart shows 310-18 uW over the whole surface.

In one embodiment, use of a dispersion optic and reflectors may change the angle of delivery to enable a periscope-like delivery of UV energy.

In one embodiment, because the delivery optics can be a flexible fiber, it can be shaped into multiple delivery forms. The optic can be used and mounted directly or with the reflector and transmissive and waterproof lens window.

Alternative embodiments may be configured for a variety of devices or target surfaces, or both. For instance, the UV disinfection device may be integrated into keyboards, push plates, monitors, kiosks, ATMs POS touch surfaces and keypads, a cell phone or a tablet, or any combination thereof.

In one embodiment, the network, communications control, and power interface of the UV disinfection device may enable ease of integration and installation. The tracking of cleaning and touches may form part of the overall disinfection process. In one embodiment, Power over Ethernet (POE) can both power the UV disinfection device and allow Ethernet communications to a secure network. In one embodiment, utilizing one or two or more security layers, the system can operate and communicate without significantly impacting communications systems. The system can also utilize USB to communicate to an external system (e.g., a computer with an API) and obtain power for powering the disinfection system. Higher power level configurations may be powered by a dedicated power supply (e.g., via a dedicated DC power connector).

In one embodiment, the integration of the periscope-like optics configuration in a keyboard may enable a self-disinfecting keyboard configuration. For instance, the electronics of the UV disinfection device can be disposed on the keyboard printed circuit board assembly (PCBA) while the optics interface to the electronics of the UV disinfection device and the UV energy may be projected at a low angle across the keyboard. In one embodiment, a direct key interface may be provided that enables deactivating zones of the keyboard as keys in those zones are pressed. The LEDs driving the optics can be divided into selectively controllable zones to deliver the UV energy to a part of the target surface of the keyboard (or another type of device as described herein). A cleaning algorithm and sensors can be provided to enable additional cleaning policy tracking and adherence.

In one embodiment, the UV disinfection device may include a reflector assembly. The reflector assembly may have complex shapes to project the UV energy substantially evenly across the target surface, such as by projecting a high percentage of UV energy to a far or distal portion of the target surface, while progressively projecting less energy as the reflection and angular relationship to the UV source gets closer to the optic or closer to a proximal portion of the target surface. This distribution may help to compensate for inverse square losses over distance from the proximal to distal portions of the target surface and may help to balance power across the target surface.

I. UV Disinfection Device

A UV disinfection device in accordance with one embodiment of the present disclosure is shown in FIGS. 1 and 2 and generally designated 100. The UV disinfection device 100 may include a support member 102 operable to facilitate mounting the UV disinfection device 100 to a device 10. The device 10 in the illustrated embodiment includes a target surface 11 having a proximal edge 13 that is proximal to the UV disinfection device 100. The target surface 11 also includes a distal edge 15 spaced apart from the UV disinfection device 100 and opposite the proximal edge 13. As described herein, the UV disinfection device 100 may distribute UV energy toward the target surface 11 to facilitate disinfection thereof.

The UV disinfection system 100 may be adapted or integrated for use with display (e.g., a 22" display). The energy distribution of UV energy over a target surface 11 of the display is depicted in FIG. 18, which shows a table of measured dosage delivery over a 12" wide by 22" high display and indicates that dosage at the two outside farthest corners is above 10 uW/cm2. The dosage over the target surface 11 may be considered in configuring the UV disinfection system 100 for an application. Time and intensity for application of UV energy may be based on the touch time and intervals. For instance, the display may interact with the UV light source (e.g., via the UV disinfection system) to assure higher usage areas are within the highest dosage areas and may also move these high touch areas around the display to eliminate fast retouching (e.g., short intervals) for consecutive users. The illustrated embodiment of FIG. 19 depicts UV intensity across the target surface 11. The higher bands of energy can be dispersed further with a reflector array configuration. The diffusion of higher intensity regions may allow for a more homogenous delivery of UV energy. A small rib at each band may enable dispersement of more energy than homogenous energy dispersal across the target surface 11.

For integration into displays, in one embodiment, the system may be built into the bezel of the display. In adapted or retrofitted configurations, in one embodiment, a display system may be similar to its configuration without UV disinfection device 100, with the display VESA mounting holes being used for holding a bracket that holds the UV disinfection 100 in place.

In the illustrated embodiment, the UV reflection chamber 120 includes a diffuser 132, and optional gel configured to provide an optical coupling between the UV energy source 134 and the diffuser 132. The optical source 134 may be disposed on a PCB 136 which may be controlled by a control assembly 150 to affect output of UV energy from the optical source 134.

The UV disinfection device 100 is shown in further detail in the illustrated embodiments of FIGS. 3-10. The UV disinfection device 100 in the illustrated embodiment includes an exit interface 110 through which UV energy may be distributed toward the target surface 11. As described herein, the UV disinfection device 100 may include one or more adjustment mechanisms 142 operable to adjust an angle of UV energy distribution relative to the target surface 11. For example, the angle of UV energy distribution may be increased or decreased based on movement of the one or more adjustment mechanisms 142.

Turning to the illustrated embodiment of FIGS. 7-10, the UV disinfection device 100 includes a UV reflection chamber 120 within which UV energy from a UV source 134 may be supplied. UV energy provided to the rear UV reflection chamber 120 by the UV source 134 may reflect off a reflector array, including one or more reflectors 122, 124, 126, toward the exit interface 110. Internal surfaces of the UV reflection chamber 120 may also be reflective to facilitate avoiding loss of energy output from the UV source 134 and directing energy toward the exit interface 110.

In the illustrated embodiment, the angle of one or more components of the UV reflection chamber 120, or the angle of the UV reflection chamber 120 itself, may be varied to affect an angle of UV energy distribution from the exit interface 110 relative to the target surface 11. For instance, in the illustrated embodiment of FIG. 7, the UV reflection chamber 120, the exit interface 110, a control assembly 150, and an upper housing 106 may be rotated about a pivot point 144 in response to adjustment of an adjuster mechanism (e.g., rotation of a screw) relative to an adjuster 140. Rotation about the pivot point 144 may enable the exit interface 110 to change in angle relative to a target surface 11 adjacent to the exit interface 110.

In the illustrated embodiment, the UV reflection chamber 120 includes a diffuser 132, and optional gel configured to provide an optical coupling between the UV energy source 134 and the diffuser 132. The optical source 134 may be disposed on a PCB 136 which may be controlled by a control assembly 152 to affect output of UV energy from the optical source 134.

The reflector array of the UV reflection chamber, as noted herein, may include one or more reflectors 122, 124, 126. The reflectors may be formed of diffusive or reflective PTI-B, diffusive or reflective Aninod, or any type of reflective material, or combination thereof. In one example, the reflectors may be configured as a coating on a fiber or plastic substrate. In another example, the reflectors 122, 124, 126 may be an extruded assembly that can be polished or coated. The reflectors 122, 124, 126 may be angled relative to each other to substantially direct UV energy received from the optical source 134 and/or the diffuser 132 toward the exit interface 110.

In the illustrated embodiment, the exit interface 110 is a light transmissive material. However, the present disclosure is not so limited. The exit interface 110 may be an aperture (e.g., air with no material through which the UV energy passes) that enables light to pass from the UV reflection chamber 120 to the target surface 11 external to the UV disinfection device.

In the illustrated embodiment, a lower housing 104 of the UV disinfection device 100 may include the support 102 to facilitate coupling to the device 10 or an object associated with a target surface 11. The lower housing 104 may remain fixed in position relative to the target surface 11, with the upper housing 106 in one embodiment being movable relative to the target surface 11 to affect an angle of distribution of UV energy.

Figure 10:
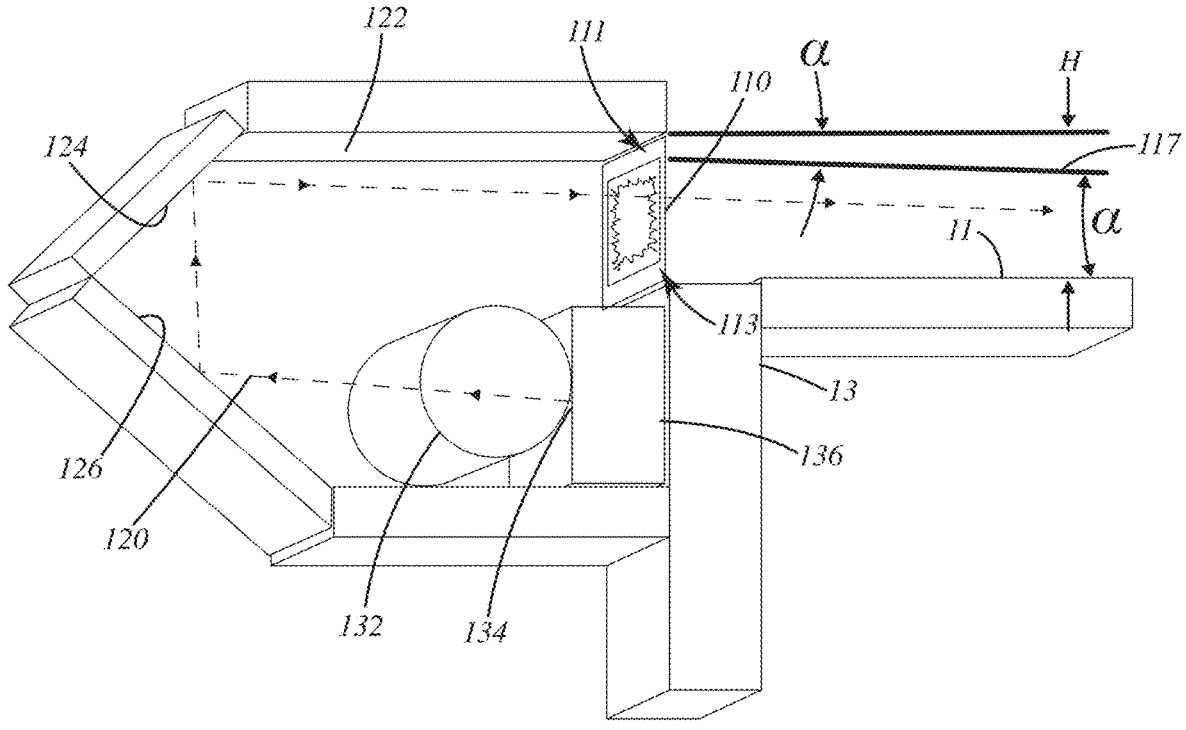
FIG. 10 shows a representative sectional view of a UV disinfection system in accordance with one embodiment.

In the illustrated embodiment of FIG. 10, the paths of UV energy emitted from the UV energy source 136 and directed toward the target surface 11 is shown in further detail. The UV energy may be directed through a diffuser 132 to facilitate spreading UV energy within the UV reflection chamber 120. The UV energy may reflect within the UV reflection chamber 120 until exiting through the exit interface 110. The UV energy, in one embodiment, may continue to reflect within the UV reflection chamber 120 until encountering the exit interface 110 at an exit angle of incidence sufficient to enable the UV energy to pass through the exit interface 110 at an angle directed toward the target surface 11. The angles of the reflectors 122, 124, 126 of the reflector array may be arranged to facilitate directing the UV energy toward the exit interface 110 at the exit angle of incidence. As described herein, the internal surfaces of the UV reflection chamber 120 may be configured to substantially prevent losses for UV energy reflecting within the UV reflection chamber 120 before the UV energy passes through the exit interface 110. For instance, one or more surfaces of the UV reflection chamber 120 may be formed of or include reflective materials (e.g., PTI-B, or Genesis Plastics Technologies: Porex Material)

In one embodiment, the UV reflection chamber 120 may be configured to direct a larger amount of UV energy at or near a distal portion 111 of the exit interface 110 relative to a proximal portion 113 of the exit interface 110. The distal portion 111 of the exit interface 110 may be disposed at a height H relative to the target surface 11 and located distal from the proximal portion 113 and the proximal edge 13 of the target surface 11. By directing a greater amount of UV energy through the distal portion 111 of the exit interface 110, a greater amount of energy may be directed toward the distal edge 15 of the target surface 11 relative to an amount of UV energy directed toward the proximal edge 13 of the target surface 11.

The angle of UV energy directed toward the exit interface 110 and/or the angle of the exit interface 110 relative to the target surface 11 may be varied to affect the angle α of UV energy directed to the target surface 11. The angle α can be seen in the illustrated embodiment of FIG. 10 relative to the target surface 11 and a plane parallel to the target surface 11 and spaced away from the target surface 11 by the height H. A boundary plane 117 may be defined by the angle α and the target surface 11, as depicted in the illustrated embodiments. UV energy may be substantially confined to a region between the boundary plane 117 and the target surface 11, thereby preventing substantial leakage of UV energy to regions of space significantly apart from the target surface 11.

In the one embodiment of the UV disinfection device 100, an exit interface 110 in the form of a small optical window is provided for treating a display surface (e.g., a target surface 11) with a low angular approach and reduced or minimal z-axis protrusion (e.g., height H relative to the target surface 11). The exit interface 110 may provide a sealed optic configuration that is resistant to water infiltration (e.g., water resistant door).

The UV disinfection device 100 may include motion sensors 109 on each end and a communication interface with the device 10 (e.g., a display). For instance, as described herein, a control system of the UV disinfection device 100 may vary operation based on a variety of parameters, including one or more states of the device 10, which may be communicated to the UV disinfection device 100 via the communication interface. The motion sensors 109 may provide feedback indicative of presence of a user relative to the target surface 11, and the UV disinfection device 100 may control operation based on this feedback.

Figure 5:
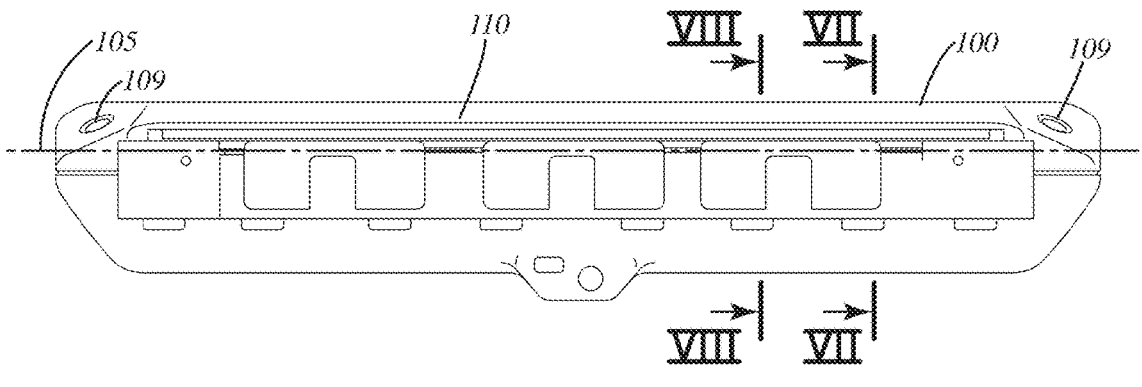
FIG. 5 shows a front view of the UV disinfection system of FIG. 3.
Figure 6:
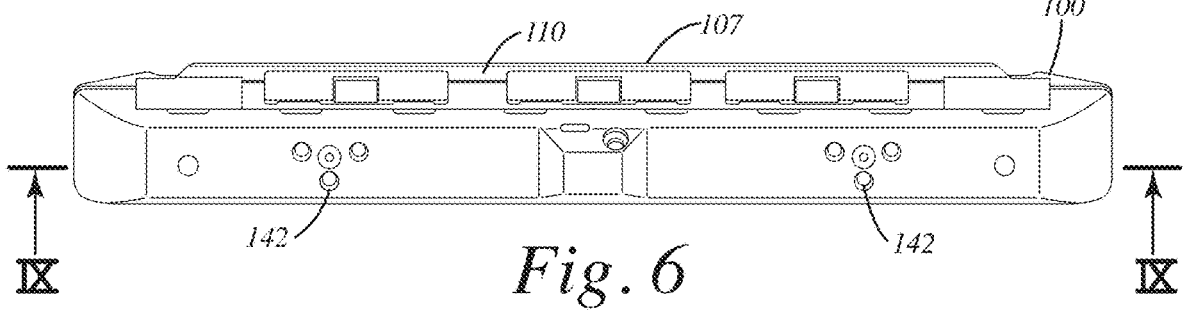
FIG. 6 shows a bottom view of the UV disinfection system of FIG. 3.

Although the UV disinfection device 100 may be configured to be adapted to a surface similar to the one depicted in the illustrated embodiment of FIG. 1, the configuration of the UV disinfection device 100 may be modular and enable integration into a variety of types of devices and components. The illustrated embodiment of FIG. 5 is an example in which the exposed surface above the dashed line 105 corresponds to a portion of the UV disinfection device that can be seen relative to the target surface 11, which is about 3-5 mm for a device 10 having a target surface that spans 560 mm from the proximal edge 13 to the distal edge 15.

The UV disinfection device in accordance with one embodiment may be operable to receive power from an external source, such as a DC source connected to the infection device via a power connector 107.

Figure 9:
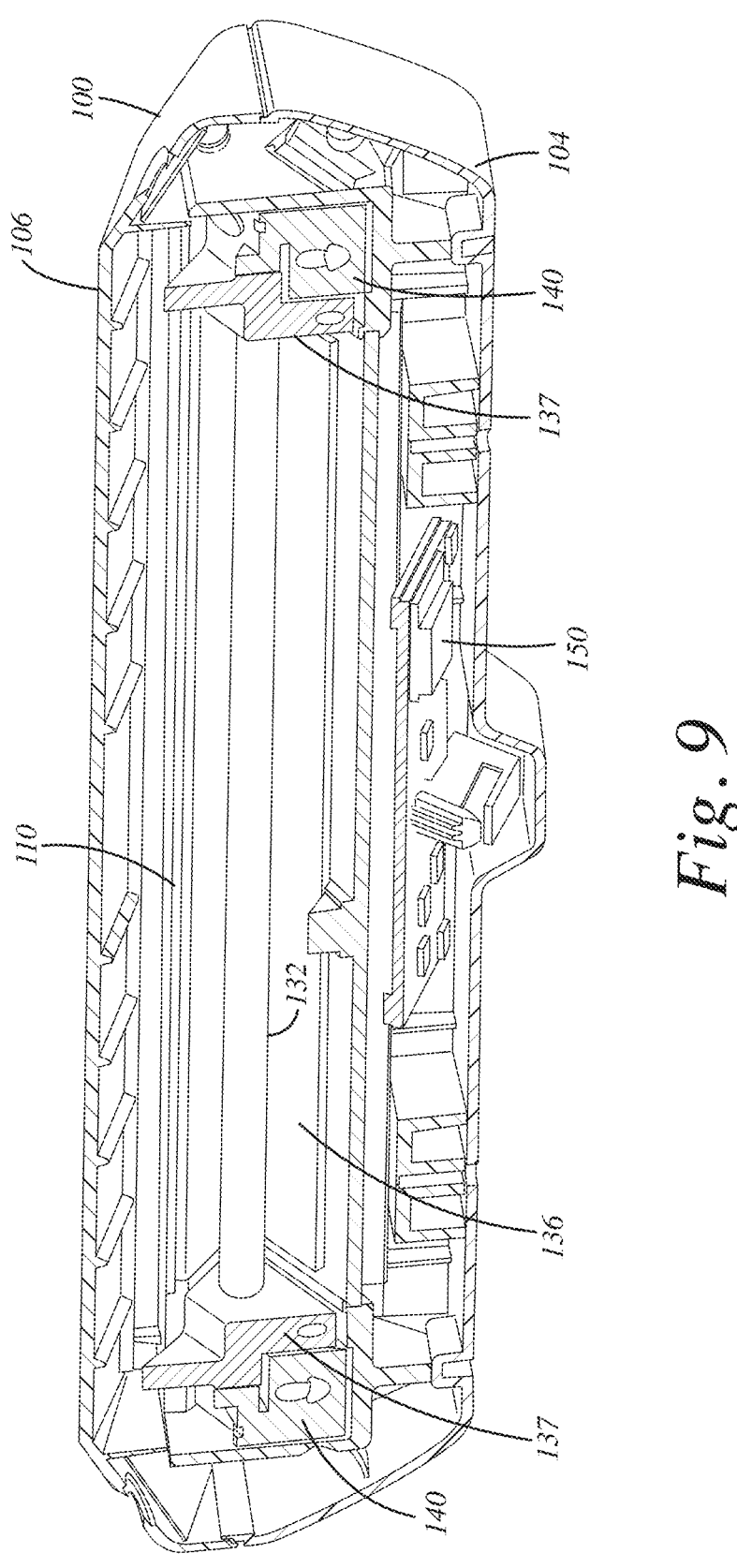
FIG. 9 shows a sectional view of the UV disinfection system of FIG. 3.

A cross section of the UV disinfection device is shown in the illustrated embodiment of FIG. 9, including depicting a cross section across the width of the optical array. A first printed circuit board assembly (PCBA) 136 of the control assembly 150 may be located under the diffuser 132, and the reflector optics or reflector array may be located on both sides of the diffuser 132 capturing the angular rays and delivering them through the lens optic (e.g., exit interface 110). A second PCBA of the control assembly 150 may be on the bottom. The sensor PCBA associated with the motion sensors 109 may be located on each end, the spacing of which may provide for maximum access to the user. The optical assembly has a rod holder 137 and an adjuster 140 for affecting an angular relationship among the exit interface 110, the UV light source 134, and the diffuser 132, and a position of the diffuser rod 132, or a combination thereof. In production, the angular position or relative position, or both, of these components may be controlled with manufacturing tolerance in a fixed position, in contrast to the configurable nature of the UV disinfection device 100 shown in the illustrated embodiment.

Figure 7:
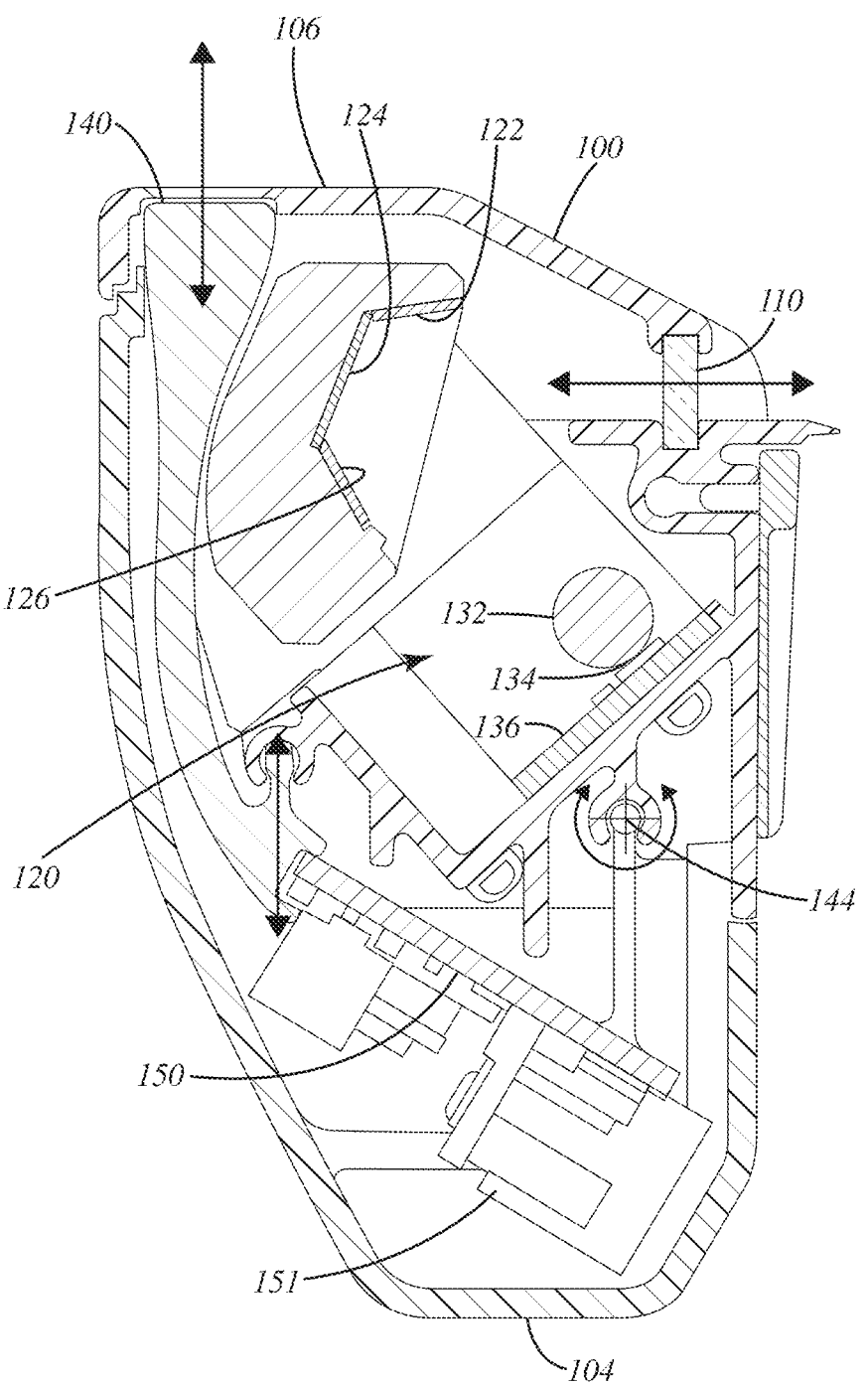
FIG. 7 shows a sectional view of the UV disinfection system of FIG. 3.
Figure 8:
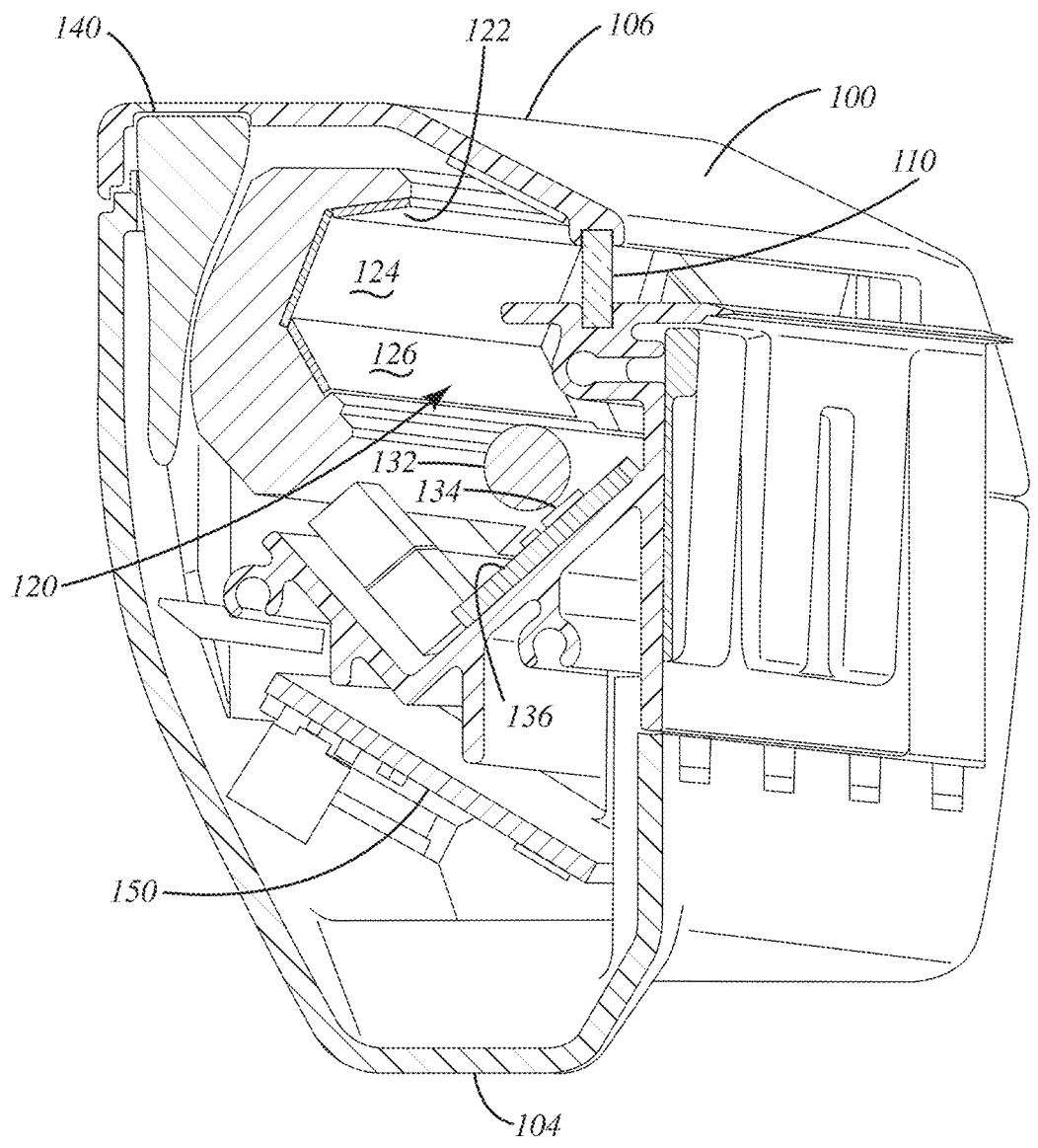
FIG. 8 shows a sectional view of the UV disinfection system of FIG. 3.

The UV disinfection device 100 in the illustrated embodiment of FIGS. 7-8 and 10 depicts a cross section edge wise across the unit showing the perpendicular relationship to the diffuser 134. The adjuster 140 can be configured to position the assembly in relationship to the exit interface 110 and the UV energy source 132 relative to the diffuser 134. A PCBA of the control system 150 and sensor PCBA 151 are also shown. The PCBA 136 for the UV energy source 134 is just below the diffuser 132 and injects the UV energy into the diffuser 132. The reflector or reflect array may then take that UV energy and shape it progressively from the farthest focal point to the nearest. The reflector may be configured for 100% reflection at the farthest end (e.g., distal end from the UV energy source 132) while being configured for 20% reflection near the UV energy source 132 depending on the energy available along the diffusion optic.

An alternative embodiment of the UV disinfection device is shown in the illustrated embodiments of FIGS. 13-17, and is similar to the UV disinfection device 100 with the exception of first and second UV disinfection devices 100 A, 100 B being disposed relative to a device 10 for disinfecting a target surface 11. The UV disinfection devices 100A, 100B may be configured similar to the UV disinfection device 100 described herein. The UV disinfection devices 100A, 100B is coupled to a device support 12 configured to device 10 in order to hold the device 10 in position relative to the UV disinfection device 100A, 100B. For instance, in the illustrated embodiments, the device support 12 includes a plurality of risers 14 operable to engage a surface of the device 10 opposite the target surface 11 to hold the device 10 in position relative to the device support 12 and the UV disinfection devices 100 A, 100 B.

Figure 17:
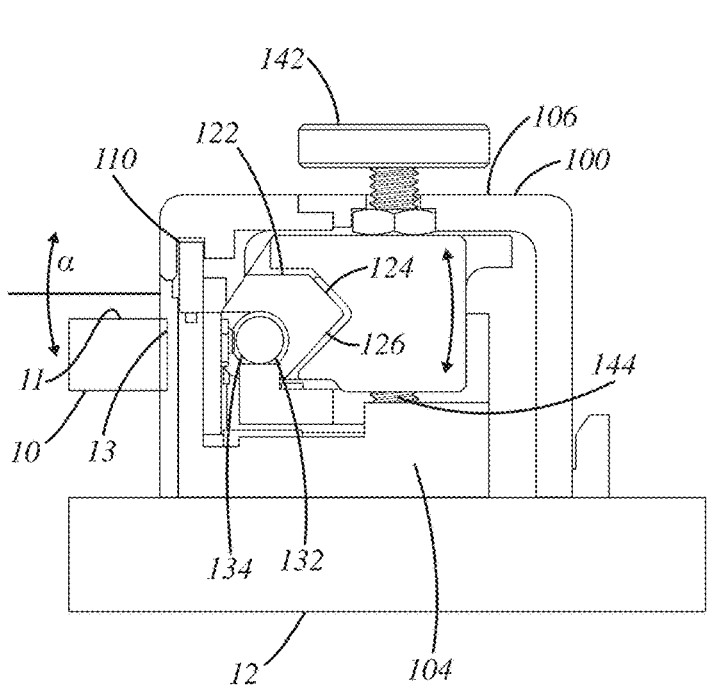
FIG. 17 shows a sectional view of the UV disinfection system of FIG. 13.

In the illustrated embodiment, the UV disinfection device 100 A, 100 B includes an adjustment mechanism 142 operable to be moved by a user (e.g., rotated by a user) to adjust the angle α of the UV energy relative to the plane defined by the target surface 11. The adjustment mechanism 142 in the illustrated embodiment of FIG. 17 is provided in the form of a thumbscrew operable to rotate in a manner that pivots the upper housing 106 of the UV disinfection device 100 B relative to a contact surface 144 for the thumbscrew 142. It is to be understood that the upper housing 106 may be adjusted or pivoted in a variety of ways and is not limited to the configuration depicted in the illustrated embodiment. For instance, the adjustment mechanism 142 may include the adjuster 140 depicted in illustrated embodiment of FIG. 7 in conjunction with the UV disinfection device 100. By pivoting the upper housing 106, the angle α may be increased or decreased relative to parallel the target surface 11. The table shown in the illustrated embodiment of FIG. 17 provides example positions (e.g., rotations) of the adjustment mechanism 142 relative to a neutral position as related to the angle α (e.g., the reflection angle of the reflector array [reflectors 122, 01 24, 126]) and a gap of the reflector array. The gap is represented by the space and angles respectively between the reflectors 122, 124, 126 and the optic 132, determining the proper optical pattern. The reflector 132 can be a coating, a reflector or a paint applied to the optic. The UV disinfection device 100 A may be configured in a similar manner but with respect to the edge 15 of the target surface 11 opposite the edge 13 proximal to the disinfection device 100 B.

Figure 26:
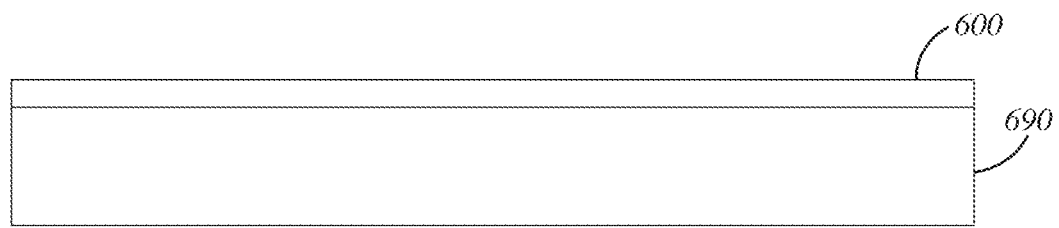
FIG. 26 shows a UV disinfection system integrated into a planar surface in accordance with one embodiment.

The UV may be incorporated into a variety of configurations and is not described to any specific type of device or target surface associated with the component, including for instance, an ATM kiosk, a keypad for outdoor use, a mobile device (e.g., a tablet or phone), a keyboard, a credit card system, a point of sale keypad, a monitor, a planar work surface (e.g., FIG. 26), and push plates and doors. Additional examples are described in PCT Appl. No. PCT/US2021/012013, entitled SYSTEM AND METHOD OF DISINFECTION, filed Jan. 2, 2021, to Baarman et al.—the disclosure of which is hereby incorporated by reference in its entirety.

Figure 29:
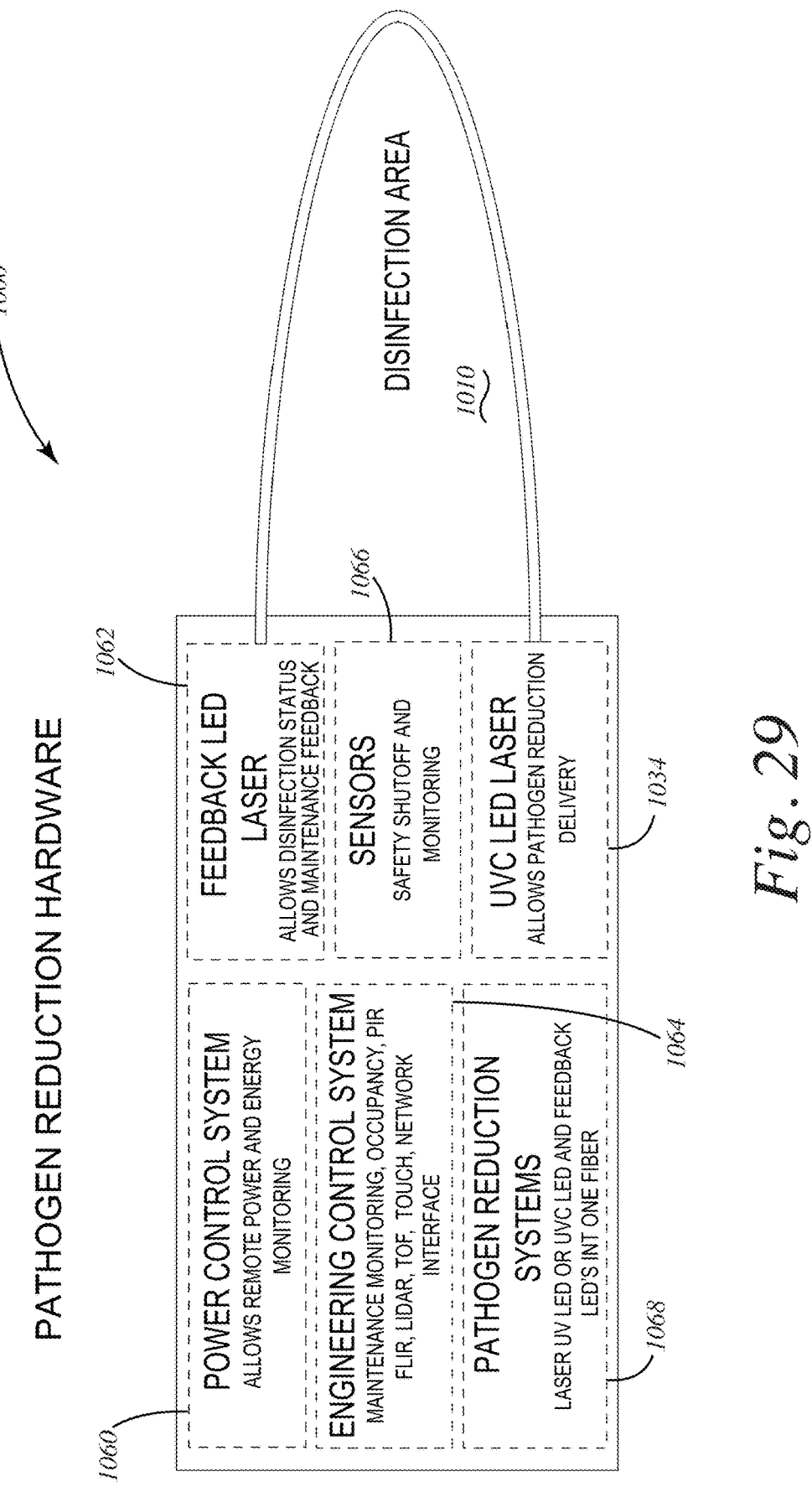
FIG. 29 shows a pathogen reduction hardware including a UV disinfection system in accordance with one embodiment.

In one embodiment, as depicted in FIG. 29, the disinfection area 1010 may be supplied UV energy by a fiber system that includes an end-lighted fiber to enable supply of energy for organic shapes and complex curves.

Example embodiments of various devices and components with a target surface are depicted in FIGS. 20-28. For purposes of disclosure, aspects of the illustrated embodiments of FIGS. 20-28 similar to the UV disinfection device 100 are identified by a reference number that shares the first two digits with the reference number provided in conjunction with the UV disinfection device 100. For instance, the UV disinfection device 200 and illustrated embodiment of FIG. 20 includes a UV energy source 234 similar to the UV energy source 134, and shares the first two digits (e.g., 34) therewith.

The device or component in the illustrated embodiments of FIGS. 20-28 is identified by reference numbers sharing the first two digits 90 (e.g., 290, 390, 490, 590, 690, 790, 890) and the target surface is identified by the first two digits 91. The proximal edge and the distal edge of the target surface are identified respectively by the first two digits 93, 95 (e.g., proximal edge 593, distal edge 595).

Figures 20, 21:
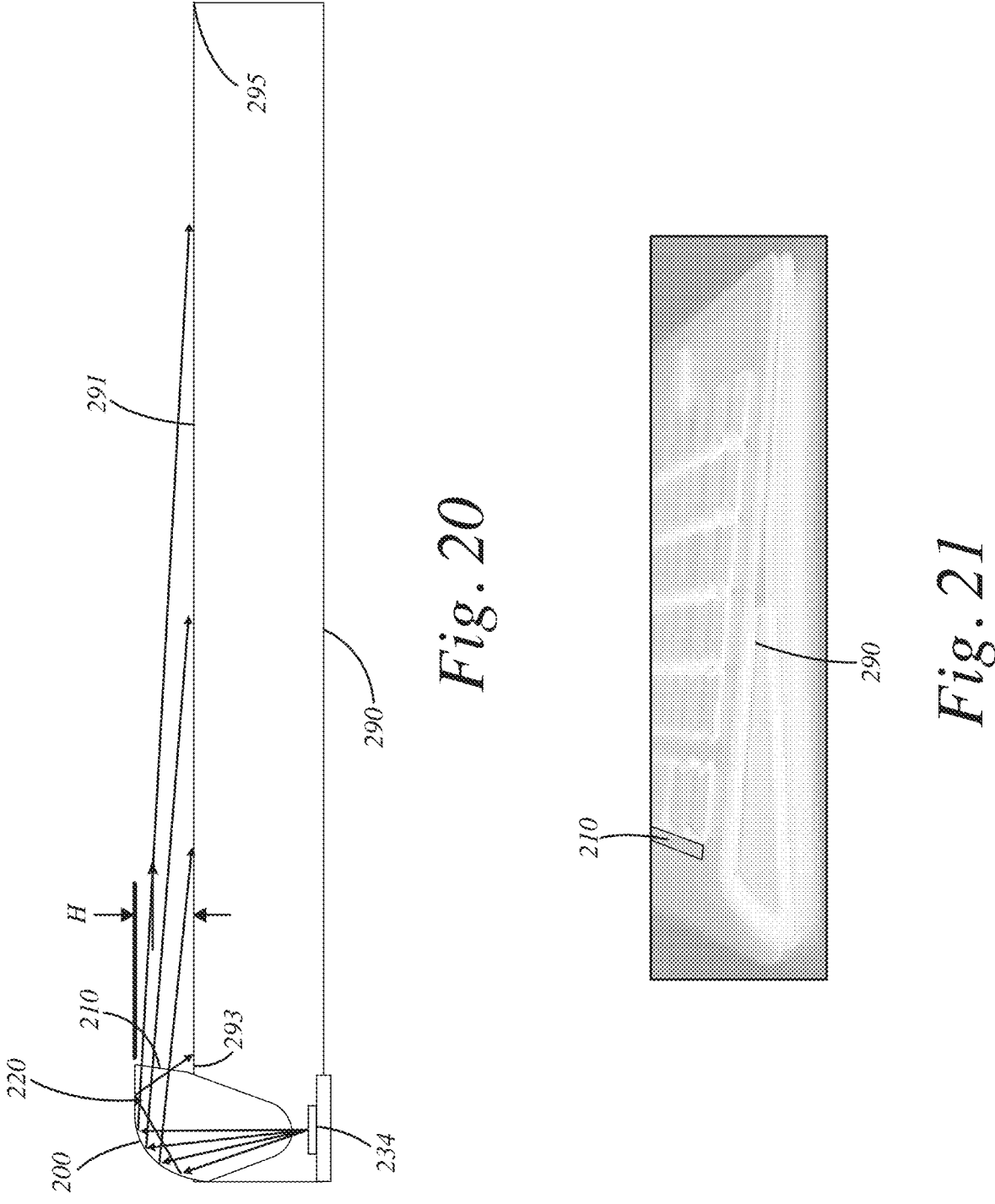
FIG. 20 shows a representative view of a UV disinfection system for a keyboard in accordance with one embodiment.
FIG. 21 shows the UV disinfection system of FIG. 20 in conjunction with the keyboard.
Figure 22:
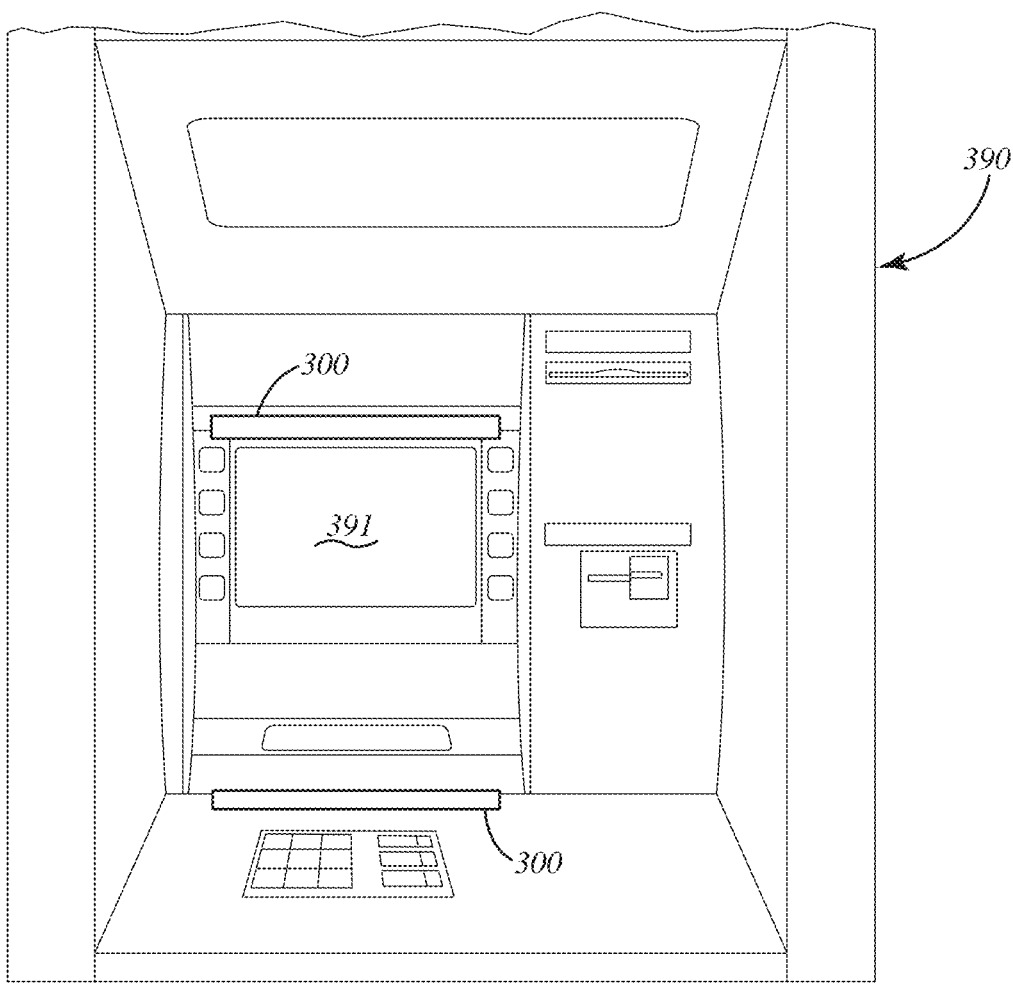
FIG. 22 shows a disinfection system and a user interface in accordance with one embodiment.

In the illustrated embodiment of FIGS. 20-21, a UV disinfection device 200 is provided in conjunction with a user interface, e.g., a keyboard, with the target surface 291 corresponding to the area associated with the keys. The height H of the exit interface 210 of the UV disinfection device 200 may be sufficiently small relative to the distance between the proximal edge 293 and the distal edge 295 of the target surface 291. As described herein, the ratio of that distance relative to the height H may be greater than five, 10, 25, 50, or 100, or a range therein. The height H in one embodiment may be 1 mm or less, while the UV disinfection device 200 may be capable of projecting UV energy through reflection chamber 220 across the target surface 291.

In the illustrated embodiment of FIGS. 22, 24-26, and 28, the UV disinfection device 300, 500, 600, 800 maybe configured to distribute UV energy across a target surface 391, 591, 691, 891. The UV disinfection device 300, 500, 600, 800 may be integrated into the device 390, 590, 690, 890. Alternatively, the UV disinfection device may be provided separate from the device and integrated into a component associated with the device (e.g., a bezel or housing associated with the device).

Figure 23:
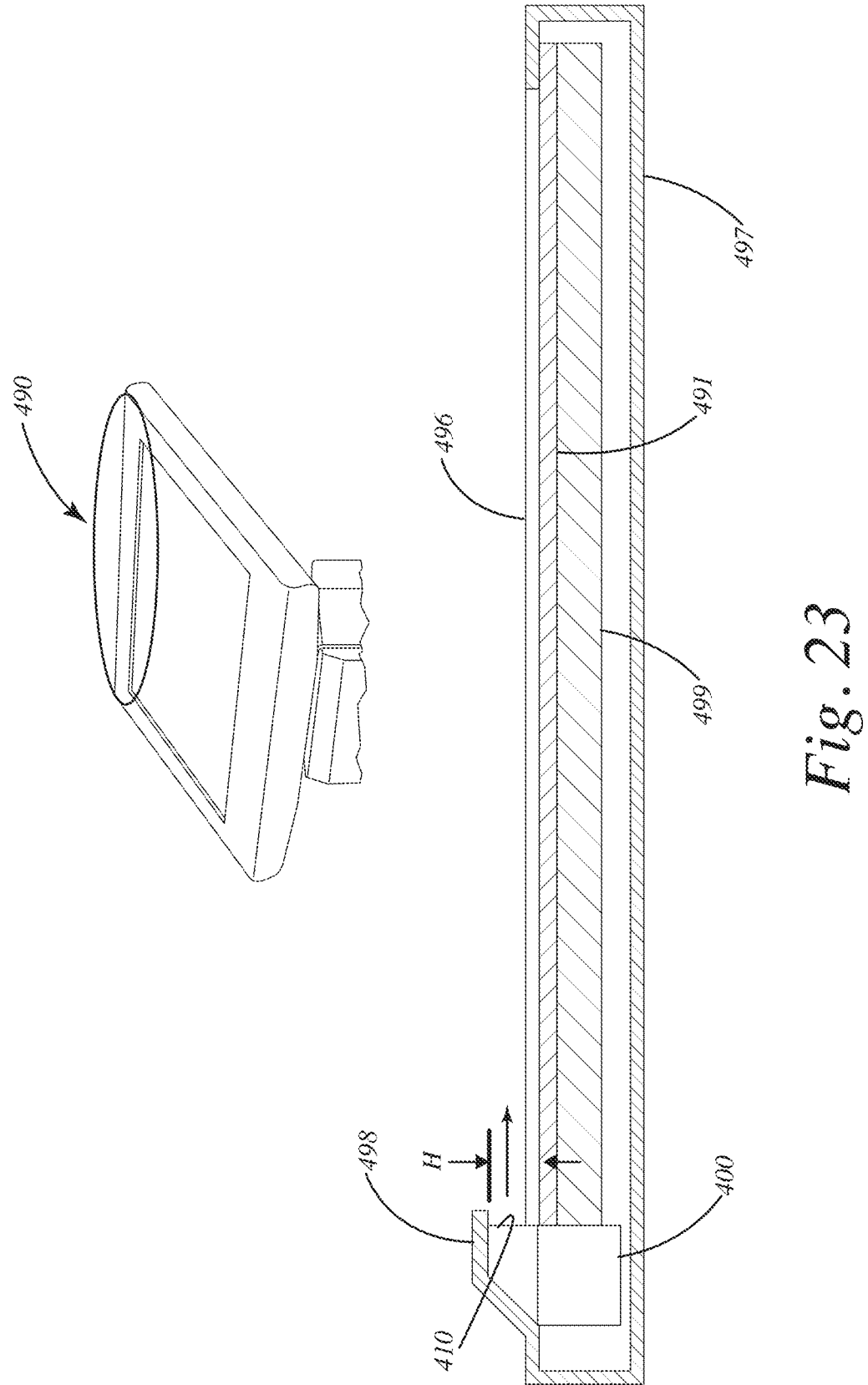
FIG. 23 shows a UV disinfection system and a display in accordance with one embodiment.
Figure 24:
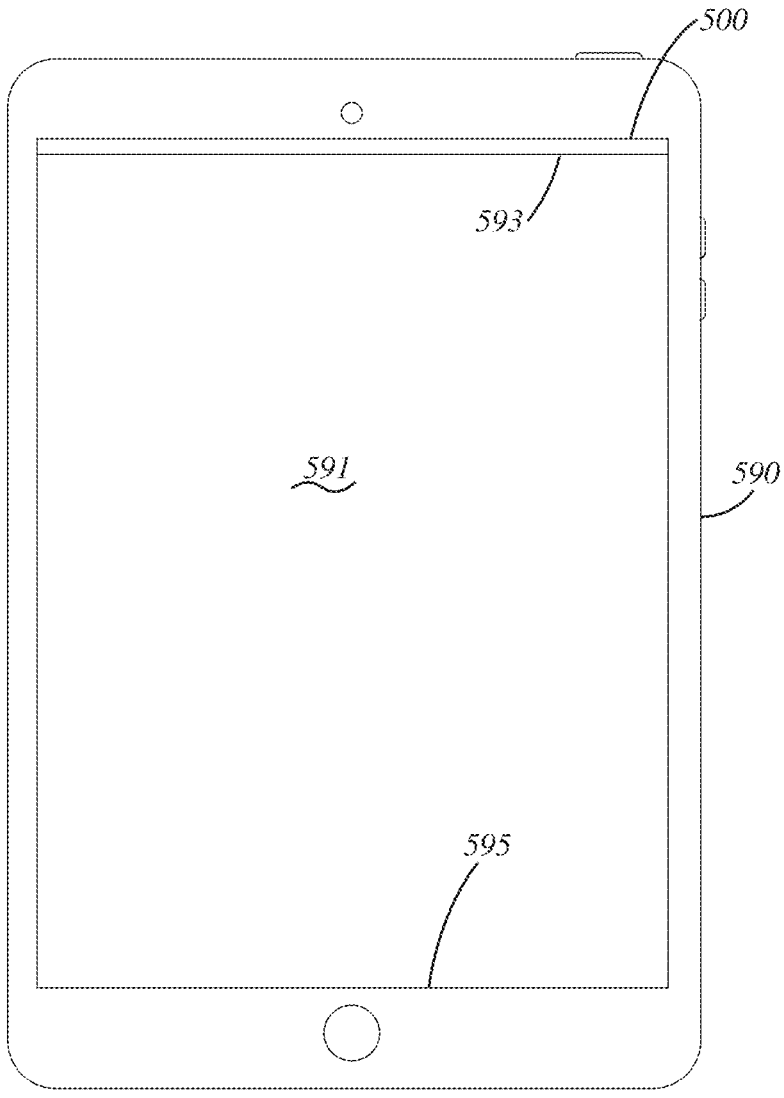
FIG. 24 shows a UV disinfection system integrated into a device in accordance with one embodiment.
Figure 25:
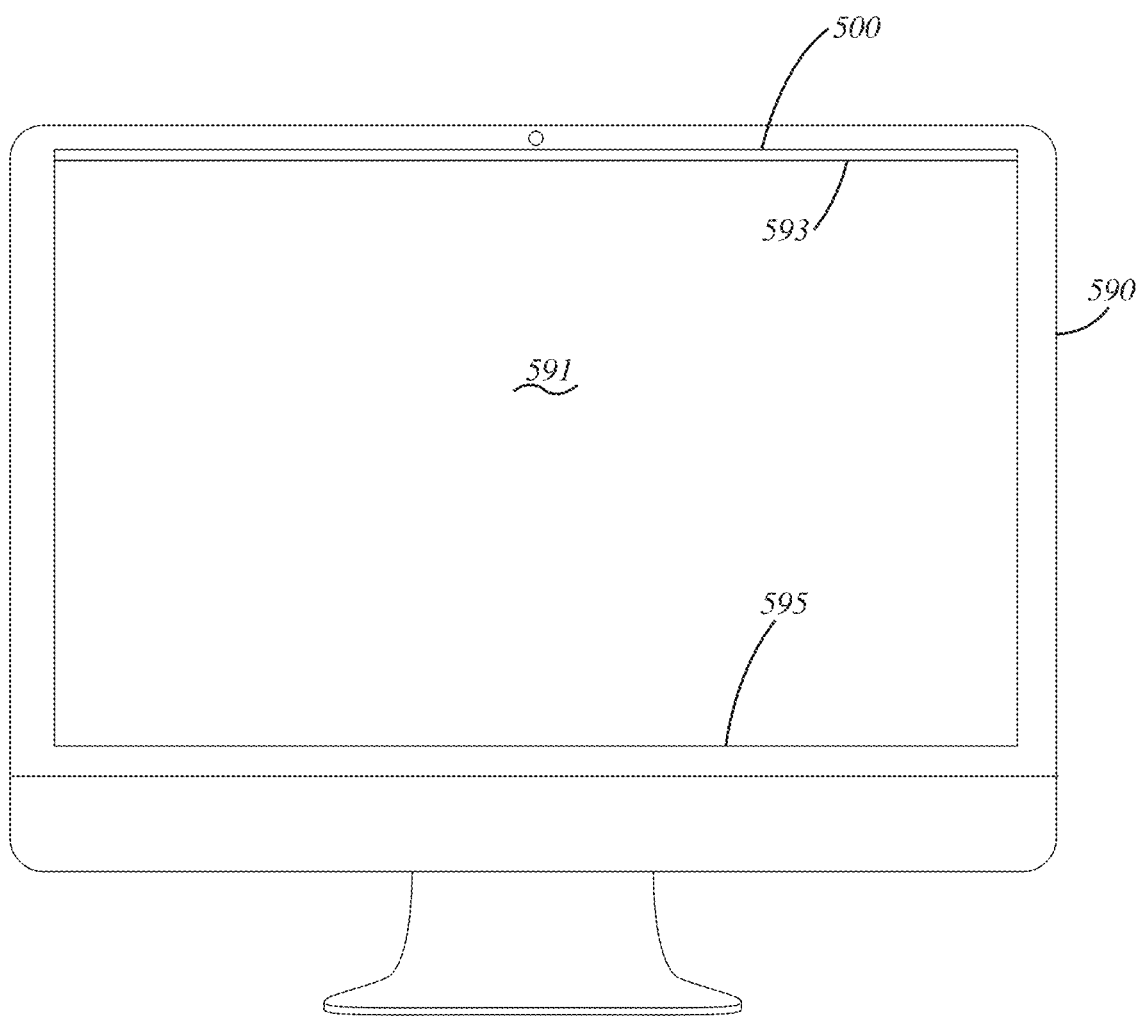
FIG. 25 shows a UV disinfection system integrated into a display in accordance with one embodiment.

For instance, in the illustrated embodiment of FIG. 23, a device 490 is provided with a housing 497 having a bezel 496 that surrounds a target surface 491 of the device 490. The electronics 499 of the device 490 may be concealed within the housing 497. The UV disinfection device 400 may also be substantially concealed within the housing 497, with the exit interface 410 being exposed for distribution of UV energy toward the target surface 491. A portion 498 of the housing 497 may be raised relative to the bezel 496 to accommodate the height H that exceeds a height of the bezel 496. A gasket portion may seal against the UV disinfection device 400 to substantially prevent water leakage near the UV disinfection device 400.

Figure 27:
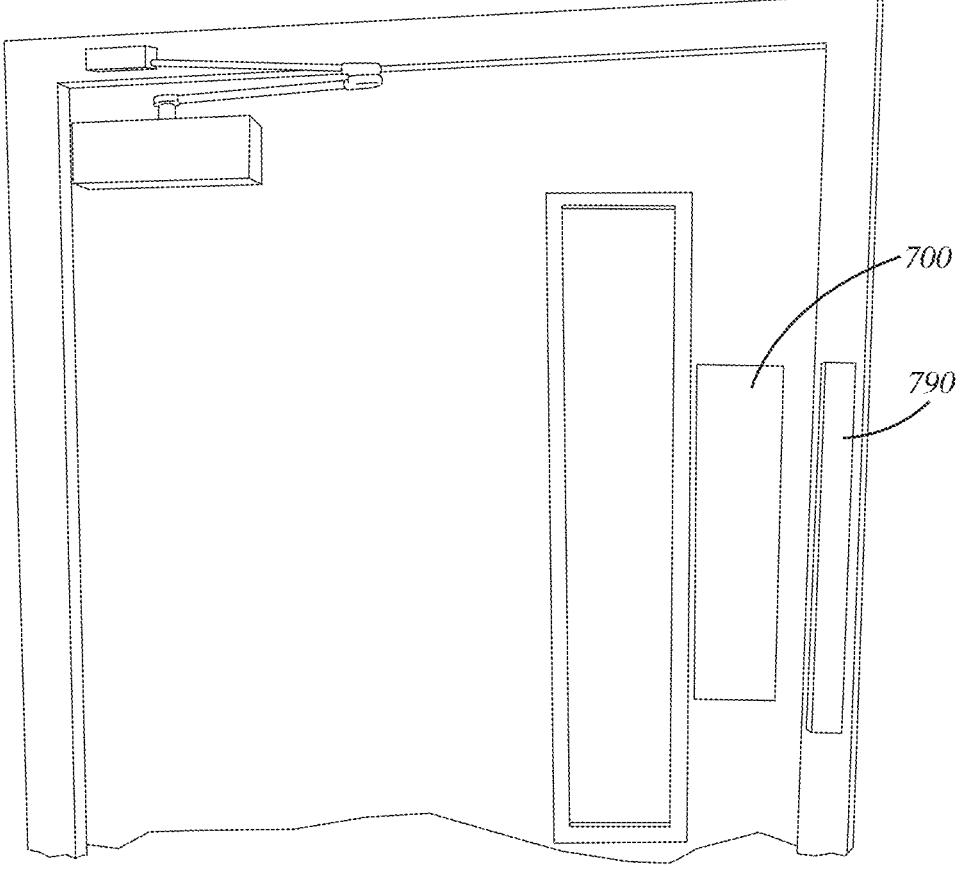
FIG. 27 shows a UV disinfection system incorporated into a door construction in accordance with one embodiment.
Figure 28:
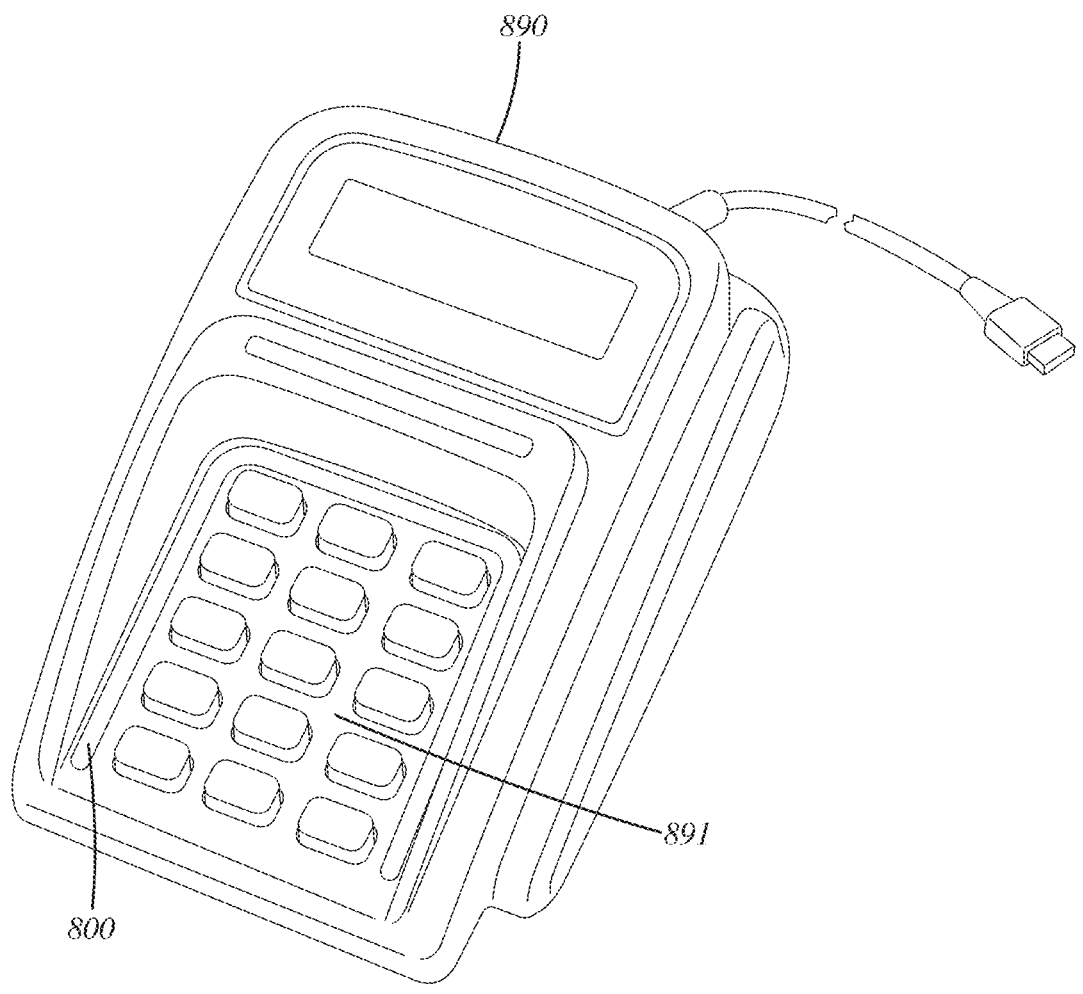
FIG. 28 shows a UV disinfection system incorporated into a point-of-sale system in accordance with one embodiment.

Turning to the illustrated embodiment of FIG. 27, as noted herein, the UV disinfection device 700 may be provided in conjunction with target surfaces of components other than devices. Further it is noted that the target surface 790 may not be directly coupled to the UV disinfection device 700. For instance, in the illustrated embodiment, the target surface 790 corresponds to a door push and the UV disinfection device 700 is disposed on a doorjamb proximal to the target surface 790 with the door in a closed position.

In the illustrated embodiments of FIGS. 7-10, the diffuser 133 may be an elongated cylindrical element having first and second opposing ends, and is operable to receive UV energy from the UV source 134 at a side between the first and second opposing ends. UV energy traverse through the diffuser 133 and exit another side between the first and second opposing ends. However, it is to be understood the present disclosure is not so limited—the configuration of the diffuser 133 and the UV source 134 may vary from application to application.

Figures 11, 12:
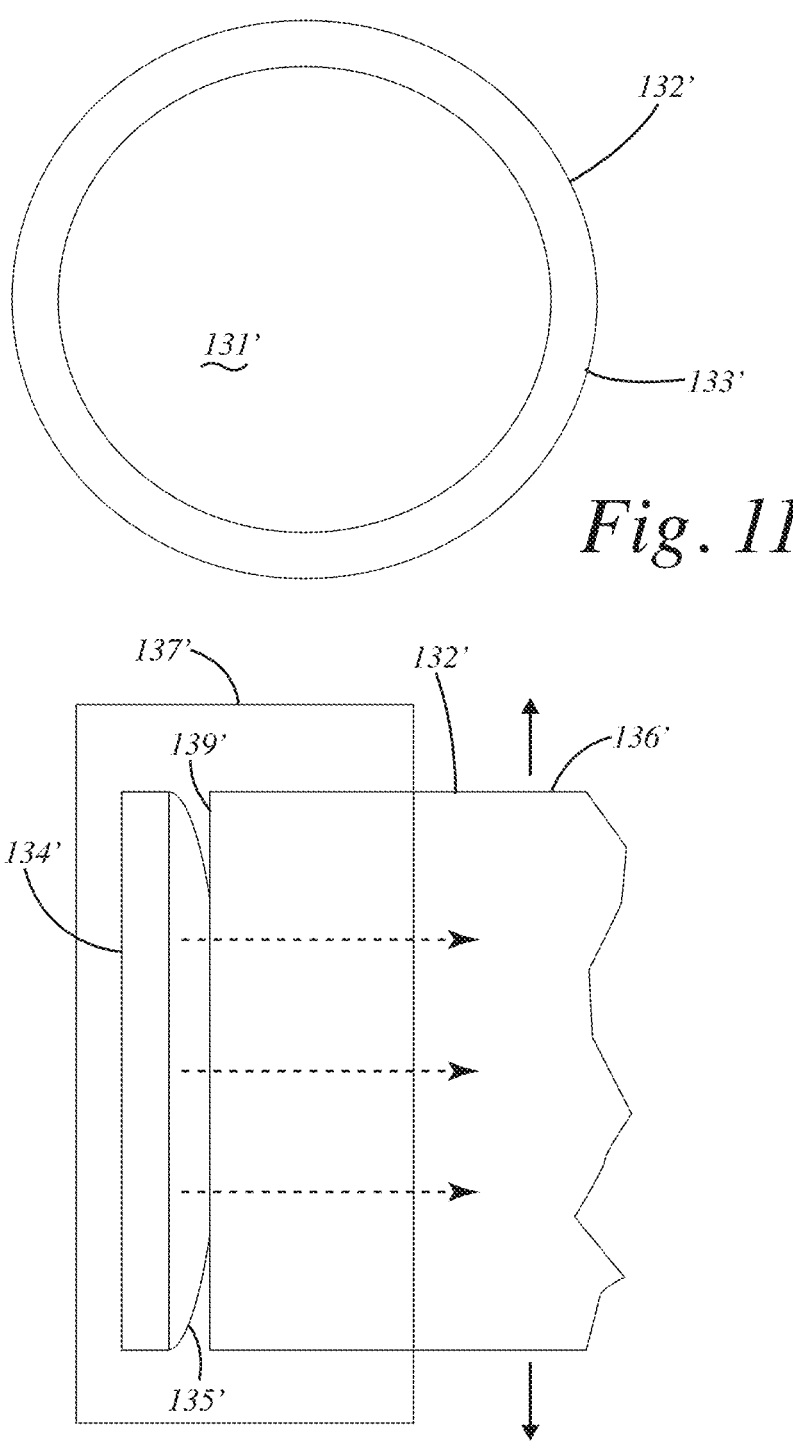
FIG. 11 shows a diffuser of a UV disinfection system in accordance with one embodiment.
FIG. 12 shows a sectional view of the diffuser of FIG. 11 in accordance with one embodiment.
Figure 13:
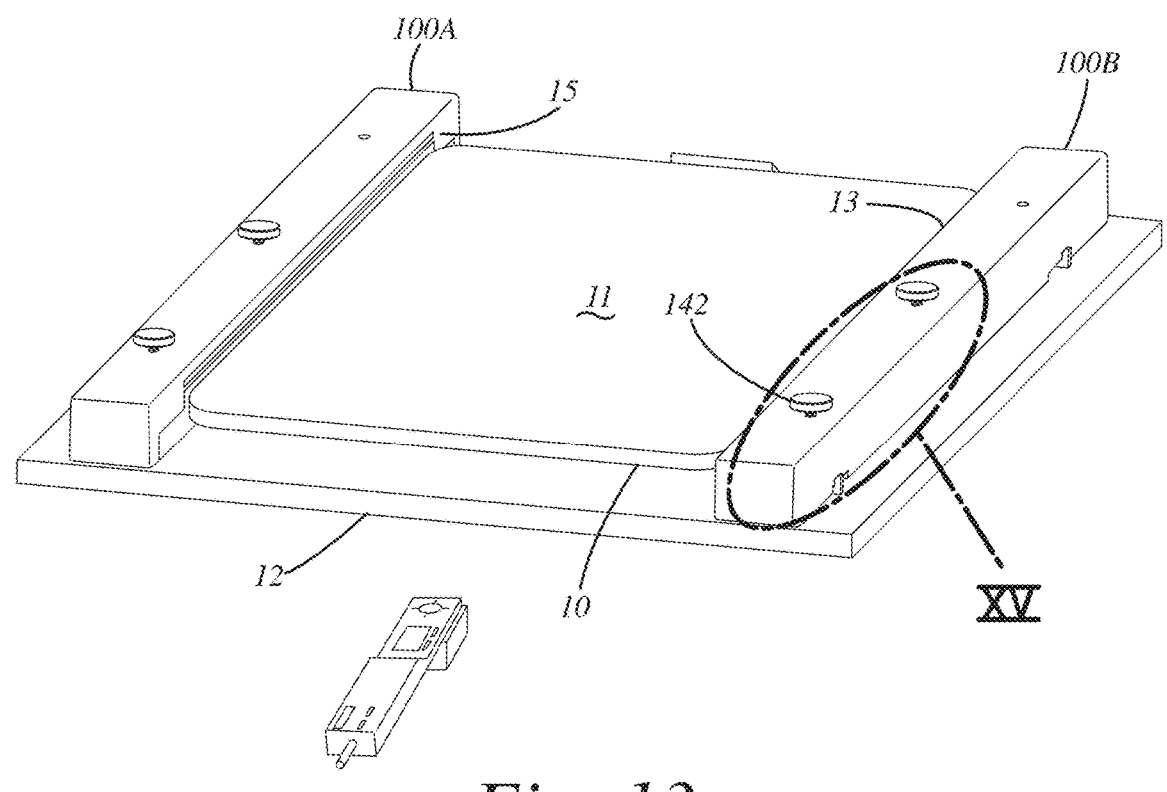
FIG. 13 shows a UV disinfection system in accordance with one embodiment in conjunction with a target surface.
Figure 14:
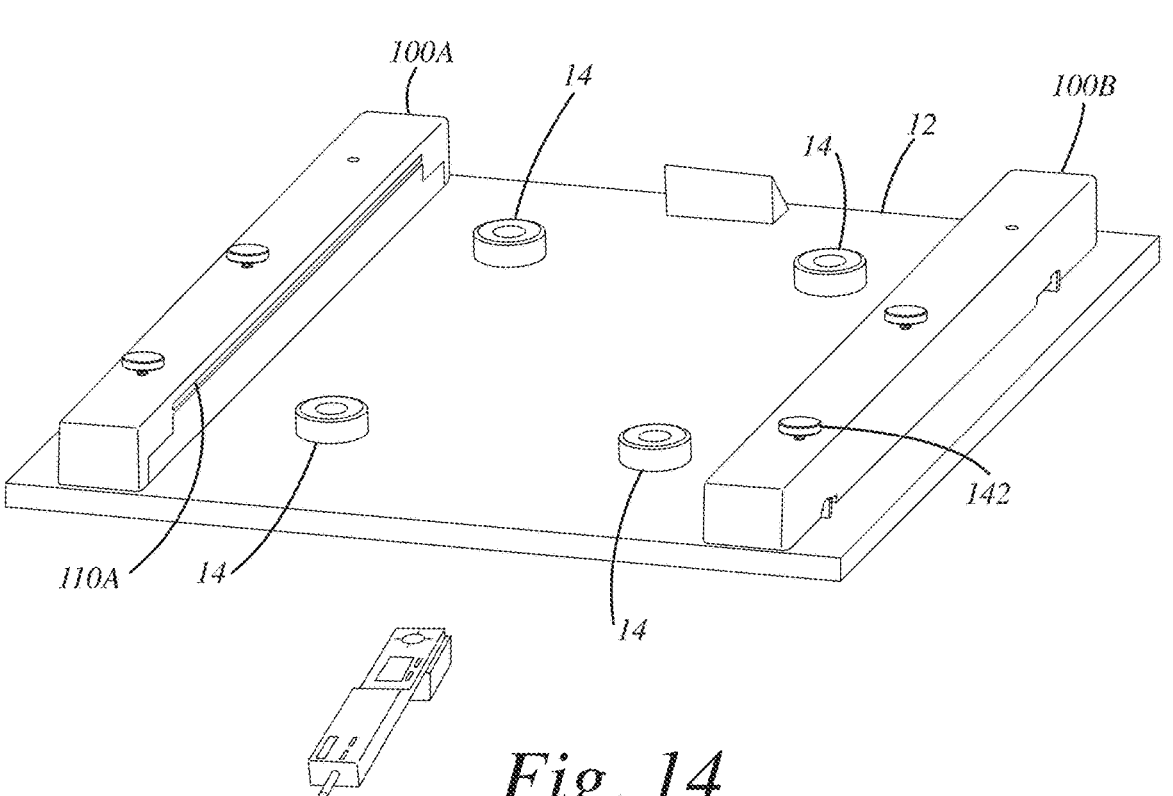
FIG. 14 shows the UV disinfection system of FIG. 13 without the target surface.
Figure 15:
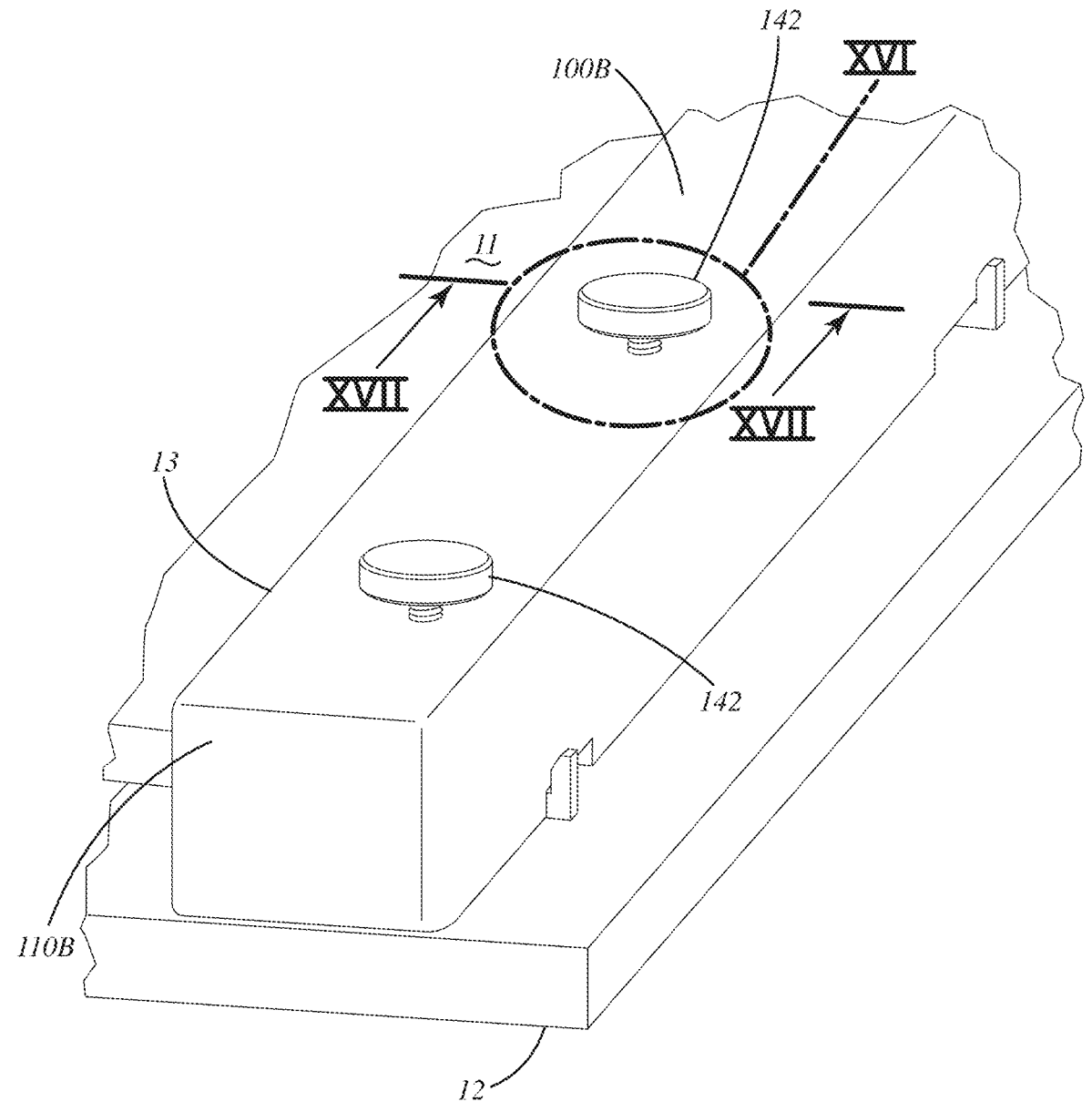
FIG. 15 shows an enlarged view of the UV disinfection system of FIG. 13.
Figure 16:
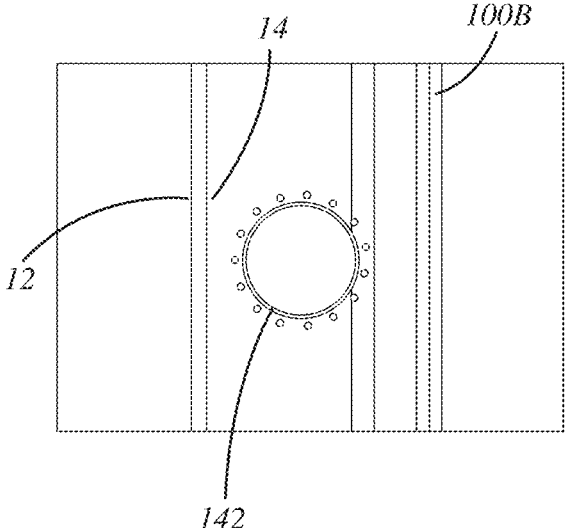
FIG. 16 shows an enlarged view of the UV disinfection system of FIG. 13.

For instance, in the illustrated embodiment of FIGS. 11-12, a diffuser 133' and a UV source 134' may be configured similar to the diffuser 133 and the UV source 134 with the primary exception that the UV source 134' is arranged to direct UV energy into the diffuser 133' via a first end 139' of the diffuser 133'. The diffuser 133' may be configured to direct the UV energy received via the first end 139' toward a side 136' into the UV reflection chamber 120. An optical gel 135' may be provided between the UV source 134' and the first end 139' to provide or enhance optical coupling therebetween. The first end 139' may be polished to further enhance optical coupling with the UV source 134'.

An optical support 137' may be provided to maintain a position or facilitate maintaining the position of the UV source 134' relative to the first end 139'. The optical support 137' may be a fiber LED interface collar in one embodiment, although it is to be understood that the optical support 137' may be configured differently. The optical support 137' may mechanically hold the UV source 134' in position relative to the first end 139', and may be configured to mechanically register the UV source 134' to the position relative to the first end 139' for optical coupling therebetween.

The diffuser 133' may include a UV transmissive side emitting a fiber element 131' surrounded by a fiber sheath 132' (e.g., a FEP fiber sheath). The fiber sheath 132' may include a side emitting coating to facilitate distributing UV energy received via the first end 139' through the side 136' of the diffuser 133'.

It is to be understood that a second UV source may be disposed relative to a second end of the diffuser 133' opposite the first end 134', such that UV energy may be provided to the diffuser 133' at both the first and second ends.

In the illustrated embodiments of FIGS. 11-12, a fiber rod (e.g., the diffuser 133') and a sheath 132' (heat shrink) may be provided. The coupling between the diffuser 133' and the UV energy source can be a polished interface. The coupling may include matching gel that increases the coupling. In one embodiment, the size of the UV energy source 134' may be substantially matched with the size of the entry point to the fiber or diffuser 132'. This may be end wise or side wise (as depicted in FIG. 10) to the fiber for different configuration options based on size and coverage options.

Alignment between the diffuser 132' and the UV source 134' may be provided in a variety of ways, depending on the configuration. For instance, in the illustrated embodiment of FIGS. 36-38, a diffuser 132" is provided in conjunction with a UV source 134". An optical support 137" may be configured to align closely with both the UV source 134" and the diffuser 132", thereby providing close alignment between the diffuser 132" and the UV source 134".

Figure 36:
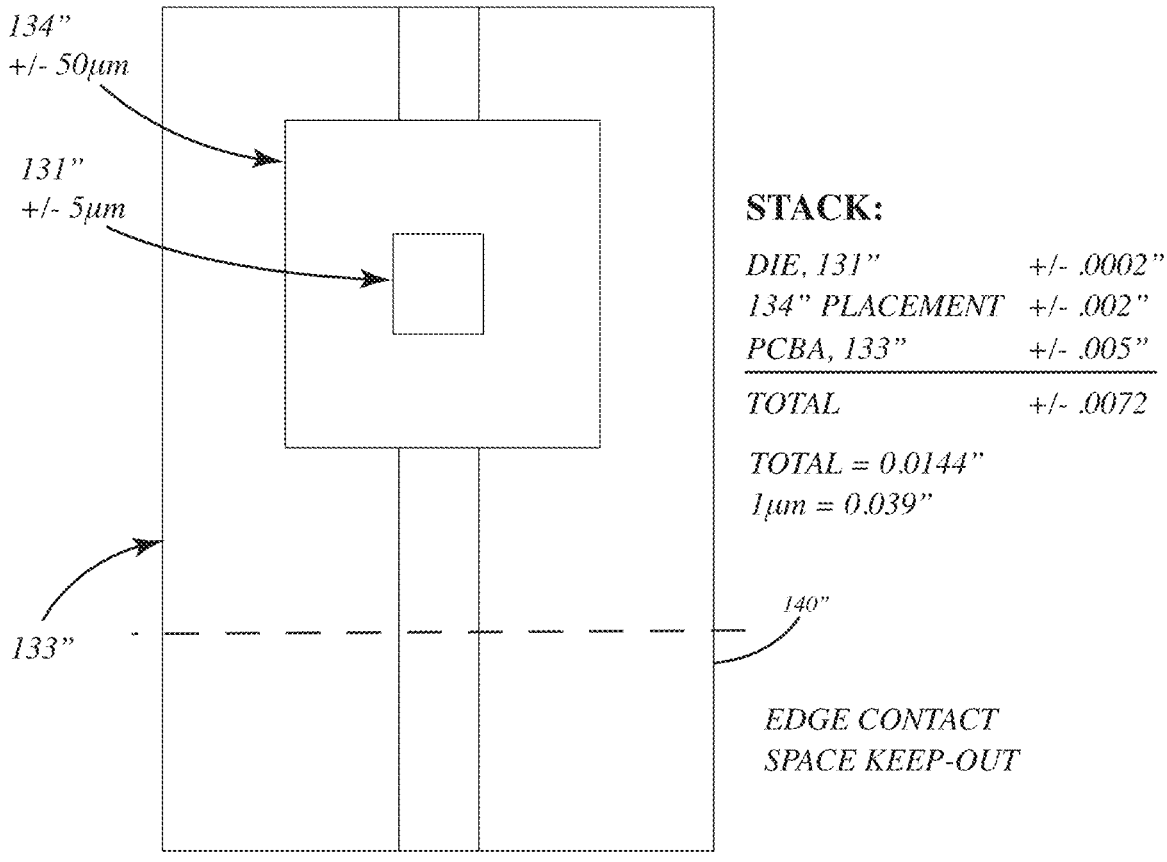
FIG. 36 an UV source and diffuser of a UV disinfection system in one embodiment, including the UV source tolerances for the assembly and the interconnect system for allowing replaceable UV sources.

In the illustrated embodiment of FIG. 36, the tolerance stackup for placement of the UV source 134" is shown with respect to a printed circuit board assembly 133" for the UV source 134". The tolerance stackup in the illustrated embodiment may provide placement tolerances for the UV source 134" that are less than +/−0.007".

The printed circuit board assembly 133" in the illustrated embodiment may be metal clad printed circuit board—however, it is to be understood that the printed circuit board may be configured differently. The manufacturing tolerances dimensions of the printed circuit board assembly" may be equal to or than +/−0.005", and optionally equal to or less than +/−0.001". As described herein, the printed circuit board assembly 133" may include a keep out area 140" configured to interface with another component for alignment of the printed circuit board assembly 133" relative to aspects of a UV disinfection system 100 in accordance with one embodiment described herein.

The UV source 134" in the illustrated embodiment includes an LED die 131" disposed on a substrate of the UV source 134". The LED die 131" may be placed with a tolerance of about +/0.0002" or 5 um, and the UV source 134" may be placed on the printed circuit board assembly with a tolerance of about +/−0.002", such that, in conjunction with a tolerance of +/−0.005" for the printed circuit board assembly 133", a total tolerance stackup of about +/−0.007 is provided.

In one embodiment, in order to provide alignment between the diffuser 132" and the UV source 134" with a tolerance better than the total stackup of the printed circuit board assembly 133" and the UV source 134", an optical support 137" may be configured to align with the UV source 134" rather than the printed circuit board assembly 133". The optical support 137" in this configuration may facilitate avoiding tolerance variation associated with the printed circuit board assembly 133" from substantially affecting alignment between the diffuser 132" and the UV source 134".

Figures 37A, 37B:
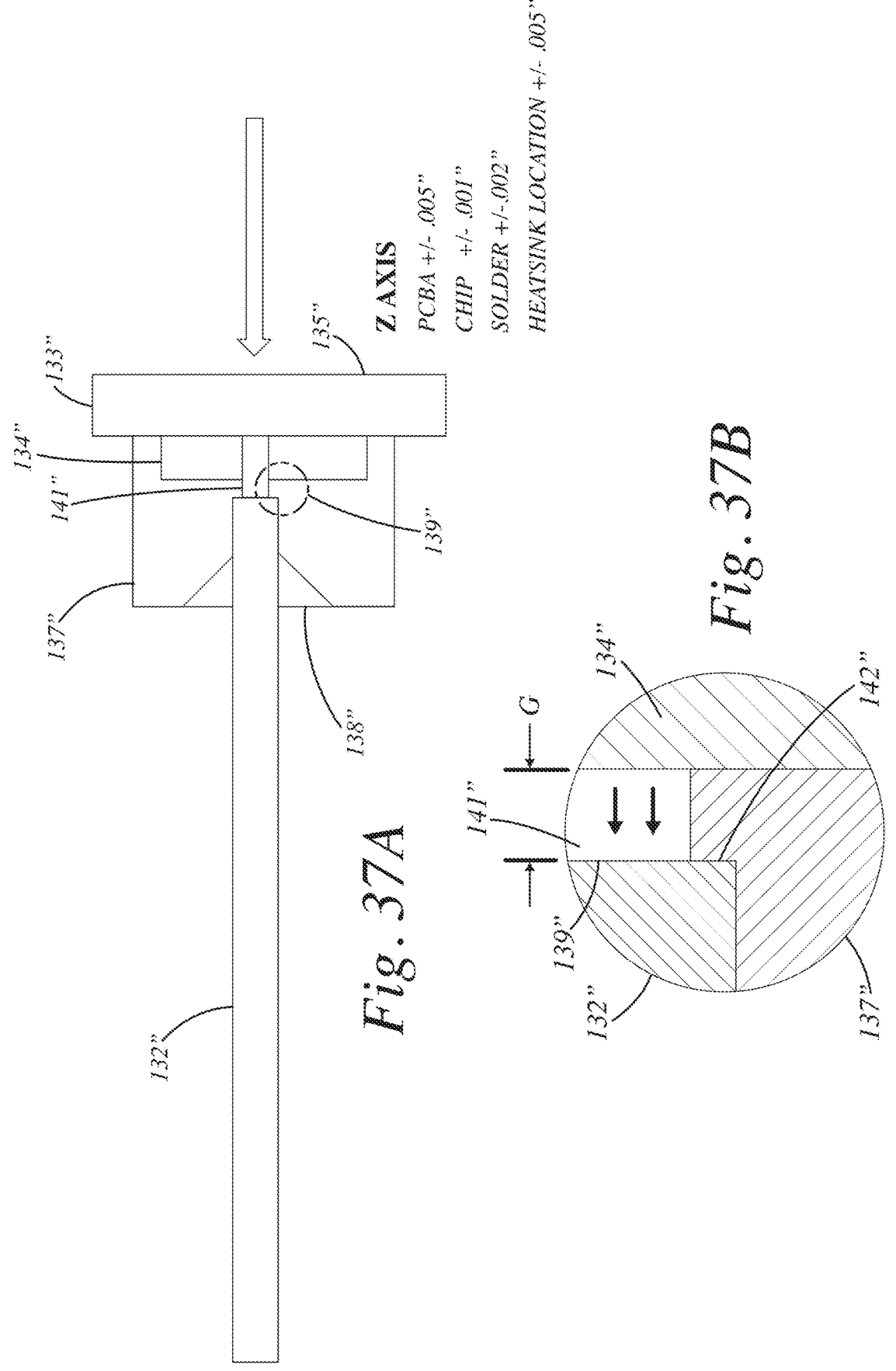
FIG. 37A shows the UV source of FIG. 36 in one embodiment along with an alignment structure mated to the diffuser (e.g., a fiber).
FIG. 37B shows an enlarged view of FIG. 37A.

In the illustrated embodiment of FIGS. 37A-B, an optical support 137" is shown in conjunction with the printed circuit board assembly 133" and the diffuser 132". The optical support 137" in includes a recess 135" configured to receive the UV source 134" and to align the LED die 131" of the UV source 134" relative to an optical channel 141" of the optical source 137" in accordance with a tolerance that is mainly dependent on the tolerances for placement of the LED die 131" and the dimensions of the UV source 134". This configuration can substantially remove affects to due tolerance variation associated with placement of the UV source 134" on the printed circuit board assembly 133" and tolerance variation in the printed circuit board assembly 133".

The optical support 137" and the recess 135" thereof may align the UV source 134" in three axes (X, Y, and Z) relative to the optical support 137". Alignment of the diffuser 132" relative to the optical support 137" may be facilitated by a diffuser receiver 138" (e.g., an LED/fiber interface) that includes a receiver portion that is larger than a seated portion to facilitate installation of the optical source 137" relative to the diffuser 132". The diffuser receiver 138" may provide a top slot configuration with Z-axis access for replacing the diffuser (e.g., an optical fiber) or the UV source 134", or both. As described herein, in one embodiment, the printed circuit board 133" may be pulled away from the optical support 137" for replacement of the UV source 134". The printed circuit board 133" may be biased toward engagement with the optical support 137" via a spring-element. The bias force may vary from application to application.

In one embodiment, the optical support 137" may provide an interface (e.g., a fiber interface) for mounting the diffuser 132" to the printed circuit board assembly 133", in a through hole registered manner or a post assembly mounted manner The receiver portion of the diffuser receiver 138" may be larger in diameter than the seated portion, and may configured to initially accept the diffuser 132" without significant effort to align the diffuser 132" with the diffuser receiver 138". As the diffuser 132" is moved toward the seated portion, the diffuser receiver 138" may be sloped to move the diffuser 132" toward close alignment with the optical support 137" in three axes. The diffuser receiver 138 may include a stop 142" of the seated portion at which the diffuser 132" is disposed in a seated position.

The stop 142" may be disposed relative to the recess 135" to define a distance or gap G between a first end 139" of the diffuser 132" and the UV source 134". It is noted that the distribution of light through the diffuser 132" is dependent on the distance (Z-axis) between the first end 139" of the diffuser 132" and the UV source 134", as well as alignment in axes (X and Y axes) orthogonal to the distance axis (Z-axis). The stop 142" may facilitate alignment of the diffuser 132" in the Z-axis and the seated portion of the diffuser receiver 138" may facilitate alignment of the diffuser 132" relative to X and Y-axes due at least in part to a close fit between the diffuser receiver 138" and the side(s) of the diffuser 132" adjacent to the first end 139".

The optical support 137" in the illustrated embodiment may be configured to enable replacement of the UV source 134" with repeatable and precise placement of the UV source 134" relative to the diffuser 132".

The UV source 134" in one embodiment may be constructed such that a life expectancy of the UV source 134" (relative to the number of uses in the UV disinfection device 100) is less than the UV disinfection device 100, itself. This life expectancy can be seen, for instance, in the illustrated embodiment of FIG. 39 and depends on a variety of factors, including the number of cycles and the number of minutes of operational time per year. For instance, in some configurations, the life expectancy of the UV source 134" is about one-year.

The optical support 138" in the illustrated embodiment may be configured to enable replacement of the UV source 134" via a new printed circuit board assembly 133". Despite variations in position of the UV source 134" among printed circuit board assemblies 133" and tolerance variations thereof, the optical support 138" may receive the UV source 134" and may enable receipt of the diffuser 132" in a manner, as described herein, that arranges the UV source 134" in position relative to the diffuser 132" both repeatably and precisely (e.g., with a tolerance for X, Y, and Z axes equal to or less than 0.001", respectively).

Figure 38:
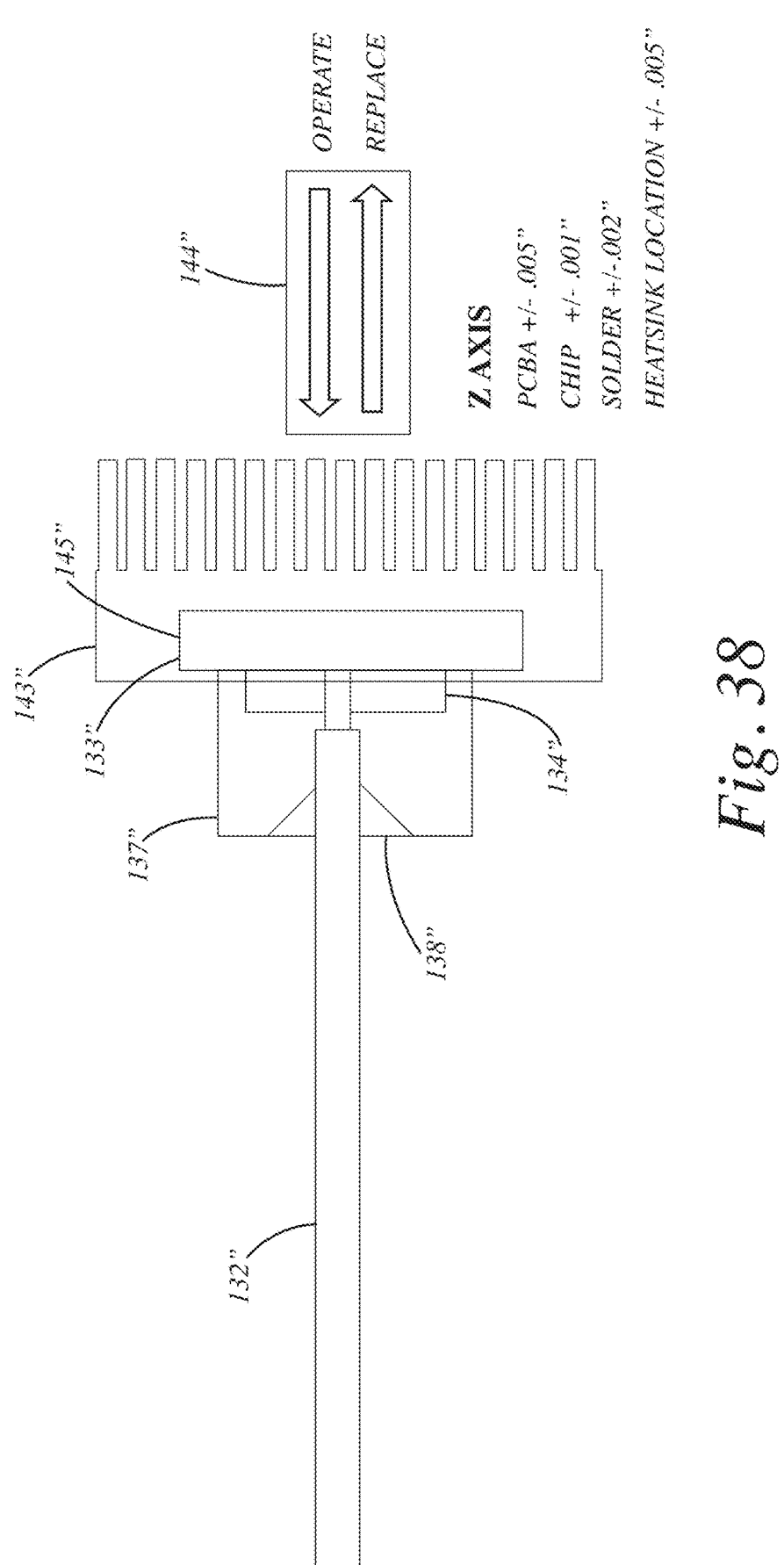
FIG. 38 shows the UV source of FIG. 36 in one embodiment along with the alignment structure mated to the diffuser and a heatsink.

Turning to the illustrated embodiment of FIG. 38, a heatsink 143" is depicted in conjunction with the printed circuit board assembly 133", the optical support 137" and the diffuser 132". The heatsink 143", in one embodiment, may include a heatsink receiver 145"(e.g., a slot) configured to receive the printed circuit board assembly 133". In the illustrated embodiment, the heatsink receiver 145" is configured to allow the printed circuit board assembly 133 "to slide in and out of the heatsink 145" that corresponds to movement in and out of the page. Although not shown, the printed circuit board assembly 133" may engage electrical contacts (e.g. contact points) in an install position with respect to the heatsink 143". In other words, with the printed circuit board assembly 133" disposed fully within the heatsink receiver 145", the printed circuit board assembly 133 may make an electrical connection with the electrical contacts to facilitate receipt of power for energizing the UV source 134". The electrical contacts may be integral to the heatsink 145" or separate therefrom. In one embodiment, the electrical contacts may be spring clips or spring-loaded pins that engage the printed circuit board assembly 133" to form an electrical connection there with. The electrical contacts may also provide a thermal path or heat dissipation or heat conduction to the heatsink 143". In the illustrated embodiments, as described herein, a spring element 144" may bias the UV source 134" into alignment with the optical support 137", such as by biasing the UV source 134" toward the optical support 137" to maintain the UV source 134 within the recess 135" of the optical support 137". The spring element 144" may interface with the heatsink 143" to bias the UV source 134", as well as the printed circuit board assembly 133". The spring element 144" may allow the heatsink 143", along with the printed circuit board assembly 133", to be separated from the optical support 137". After separation, the printed circuit board assembly 133", including the UV source 134", may be replaced. The heatsink 143" and the new printed circuit board 133" may be repositioned for receipt by the optical support 137" and held or biased in the received position by the spring element 144". As described herein, the bias force provided by the spring element 144" may vary from application to application.

In the illustrated embodiment of FIG. 38, the heatsink 134 is connected to a light-pipe that is connected to the printed circuit board assembly 133".

II. Pathogen Reduction Hardware and Systems

The UV disinfection device in accordance with one embodiment may be incorporated into a pathogen reduction system, such as a system described in PCT Application No. PCT/US2021/021629, entitled DISINFECTION TRACKING NETWORK, filed Mar. 10, 2021, to Baarman et al.—the disclosure of which is hereby incorporated by reference in its entirety. The UV disinfection device provided as a pathogen reduction hardware is depicted in the illustrated embodiment of FIG. 29 and designated 1000. The pathogen reduction hardware 1000 may include a UV energy source 1034 operable to generate UV energy for disinfecting a target area or target surface 1010. The pathogen reduction hardware 1000 may include a power control system 1060, a feedback system 1062, and control system 1064, and an interface to one or more pathogen reduction systems 1068 integrated or external to the pathogen reduction hardware 1000.

The power control system 1060 may interface with a power management system operable for controlling and powering the pathogen reduction hardware 1000 1000. The power control system 1060 may receive power or communication, or both, with the power management system and directives relating to operation.

The feedback system 1062 may be operable to provide feedback to a user with respect to information pertaining to operation of the pathogen reduction hardware 1000. For instance, the feedback system 1062 may include one or more colored indicators (e.g., LEDs) operable to selectively turn on and off based on a status of the pathogen reduction hardware 1000. The feedback system 1062 may provide information with respect to disinfection status or maintenance feedback, or a combination thereof.

The control system 1064 in the illustrated embodiment is operable to control operation of the pathogen reduction hardware 1000. The control system 1064 may be configured to control operation absent directive from external devices, or based on directive from external devices, or a combination thereof. The control system 1064 may be operable to communicate information external to the pathogen reduction hardware 1000, such as status information pertaining to operation, or an area associated with the pathogen reduction hardware 1000 (e.g., presence or use of the area). The control system 1064 of the illustrated embodiment may provide or obtain, or both, maintenance monitoring and occupancy information. The control system 1064 may include a forward-looking infrared system (FLIR), a passive infrared system (PIR), a light detection and ranging (Li-DAR) system, a time-of-flight (TOF) determination system, a network interface, or a combination thereof.

The sensor system 1066 in the illustrated embodiment may be operable to detect one or more characteristics pertaining to the pathogen reduction hardware 1000, including, for example, operational aspects of the UV energy source 1034. Additional examples include aspects described in conjunction with the control system 1064 including the FLIR, PIR, LiDAR, and TOF systems, which may be incorporated into the sensor system 1066 rather than the control system 1064. The sensor system 1066 may be in communication with the control system 1064 to provide feedback pertaining to sensed information. In the illustrated embodiment, the sensor system 1066 may generate sensor information pertaining to monitoring and enhancing safety shutoff measures related to operation.

The pathogen reduction systems 1068, as described herein, may be integrated or separate from the pathogen reduction hardware 1000. For instance, the pathogen reduction hardware 1000 may include more than one UV disinfection device in accordance with one embodiment. The pathogen reduction hardware 1000 in one embodiment may include more than one UV disinfection device that share a common UV energy source 1034.

In the illustrated embodiment, the pathogen reduction system 1068 may include a laser UV energy source and feedback systems integrated or shared by one or more fibers for distribution of energy.

A low profile optical delivery system in one embodiment may be configured to limit the exposure to the user. By maintaining UV energy in such a low angle to the display (e.g. the target surface), UV exposure may be limited to within millimeters of the target surface. This limited exposure may enhance safety of the system. The low angle also has a terminus where the angle is limited to a distance along the surface. In other words, the low angle may provide a terminus that defines the farthest target distance on the treatment surface at which UV energy is provided. Beyond that terminus, the optics may be configured to limit or terminate UV beyond that point. This configuration may enhance protection for the user from odd angles or the potential of eye contact. The low angle and specific low angle pattern may enhance the safety profile of this system. The reflector, the treatment window, and the optic may be configured to be specific in the delivery of UV energy. Although UVC may be utilized for greater performance, the present disclosure is not so limited—white light, pulsed white Zenon, UVA, UVB or ratios thereof may be utilized in addition to or alternative to UVC. These other sources may provide pathogen reduction.

A power management system may be provided in accordance with the present disclosure for controlling and powering the UV disinfection device. The system can include UV disinfection devices, including disinfection devices other than the UV disinfection device described herein. For example, separate air pathogen reduction hardware modules can be provided throughout a room. Each of these air pathogen reduction hardware modules can include one or more different systems therein, such as one or more power control systems 1060, one or more engineering control systems 1064, and one or more pathogen reduction systems 1068.

Figure 30:
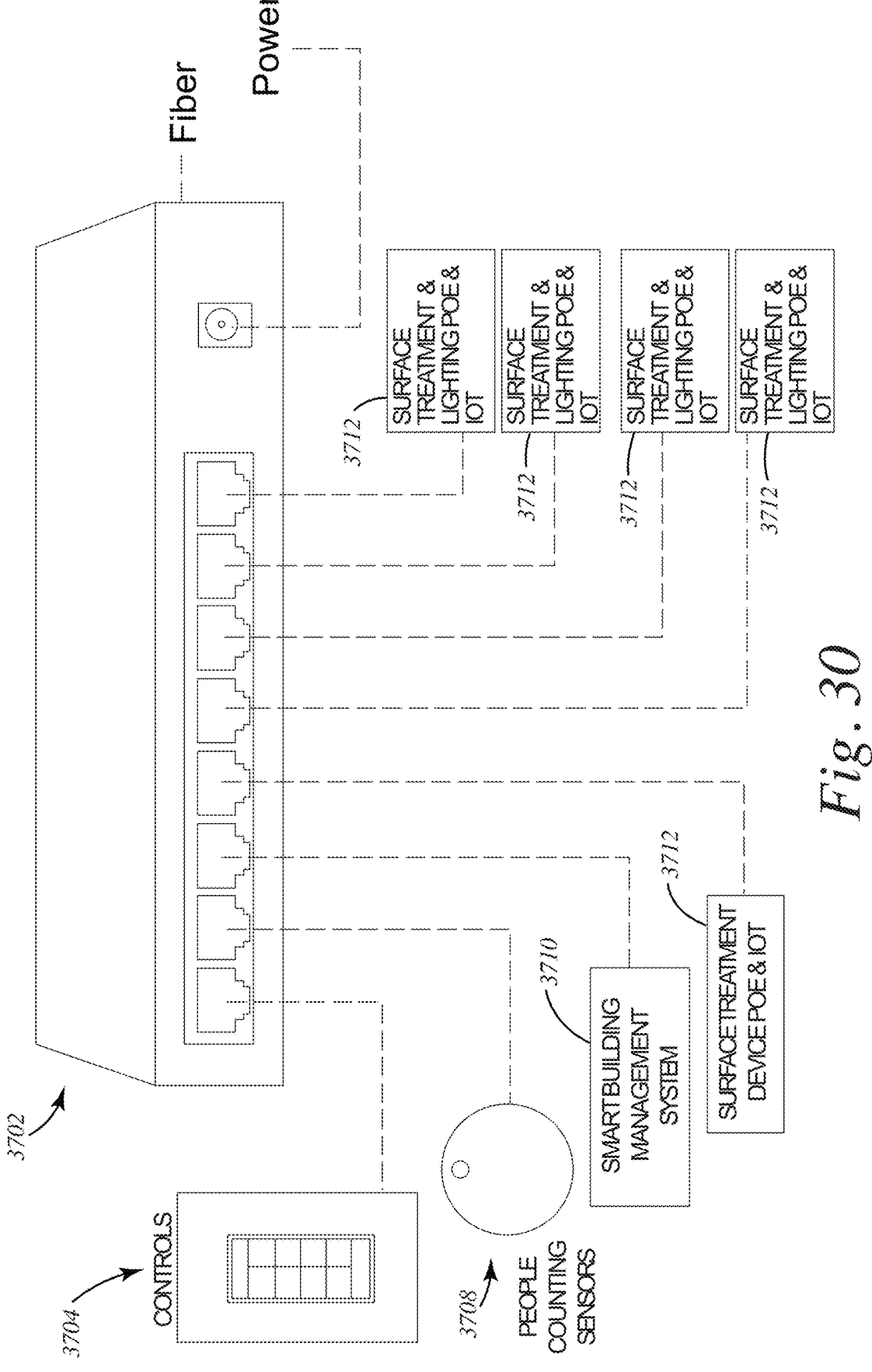
FIG. 30 shows a communication and power distribution system for a UV disinfection system in accordance with one embodiment.

One example of a network interface 3702 and associated topology that can be utilized in connection with a power management system of the present disclosure is illustrated in FIG. 30. Power over Ethernet generally describes any standard or ad hoc system that passes electric power along with data on Ethernet cabling. The network interface 3702 depicted in this embodiment has eight ports, five POE ports and three communication ports that provide communication but do not provide Power over Ethernet. In alternative embodiments, the network interface may have additional or fewer POE ports and communication ports. The network interface 3702 includes a power input that can be connected to mains power or another power source. The network interface 3702 also includes an inbound network connection, such as a fiber Internet connection that enables the network interface to communicate with cloud based services or with other remote servers or computers.

The POE network interface ports allow a single cable to provide both data connection and electric power to devices. In the depicted embodiment, power and communication can be provided to surface treatment devices 3712. The POE connections can be provided as a supplement or instead of the multi-drop controller connections. In some situations, certain devices may only receive power or may only receive communication. In other situations, all devices both receive power and are capable of communication over the network. The POE can be provided via IEEE 802.3 such as alternative A, alternative B, 4PPoE standards, or essentially any other POE type protocol.

Via this network interface 3702, network connections can be provided to the various local devices, for example various devices located around a room. For example, several different combinations of surface treatment modules 3712 can be installed throughout a room and connected via POE in order to make each module a separate, individually addressable Internet of Things device. The controls in the room 3704 can be programmed to control the certain designated devices in unison or to control one or more devices individually. The smart building management system can also be in communication with the system and can issue commands to the various devices via the network as well as receive reports regarding disinfection and other information available from the surface treatment devices 3712, sensors, controls, or any other equipment connected to the POE network interface 3702.

The network interface can be connected to various sensors, such as a people counting sensor 3708 that can count the number of people in proximity of the sensor. The tracking information can be relayed through the network interface to a cloud server. The data can be utilized to improve disinfection and disinfection cycle interruption recovery strategies.

III. Method of Operation

Figure 31:
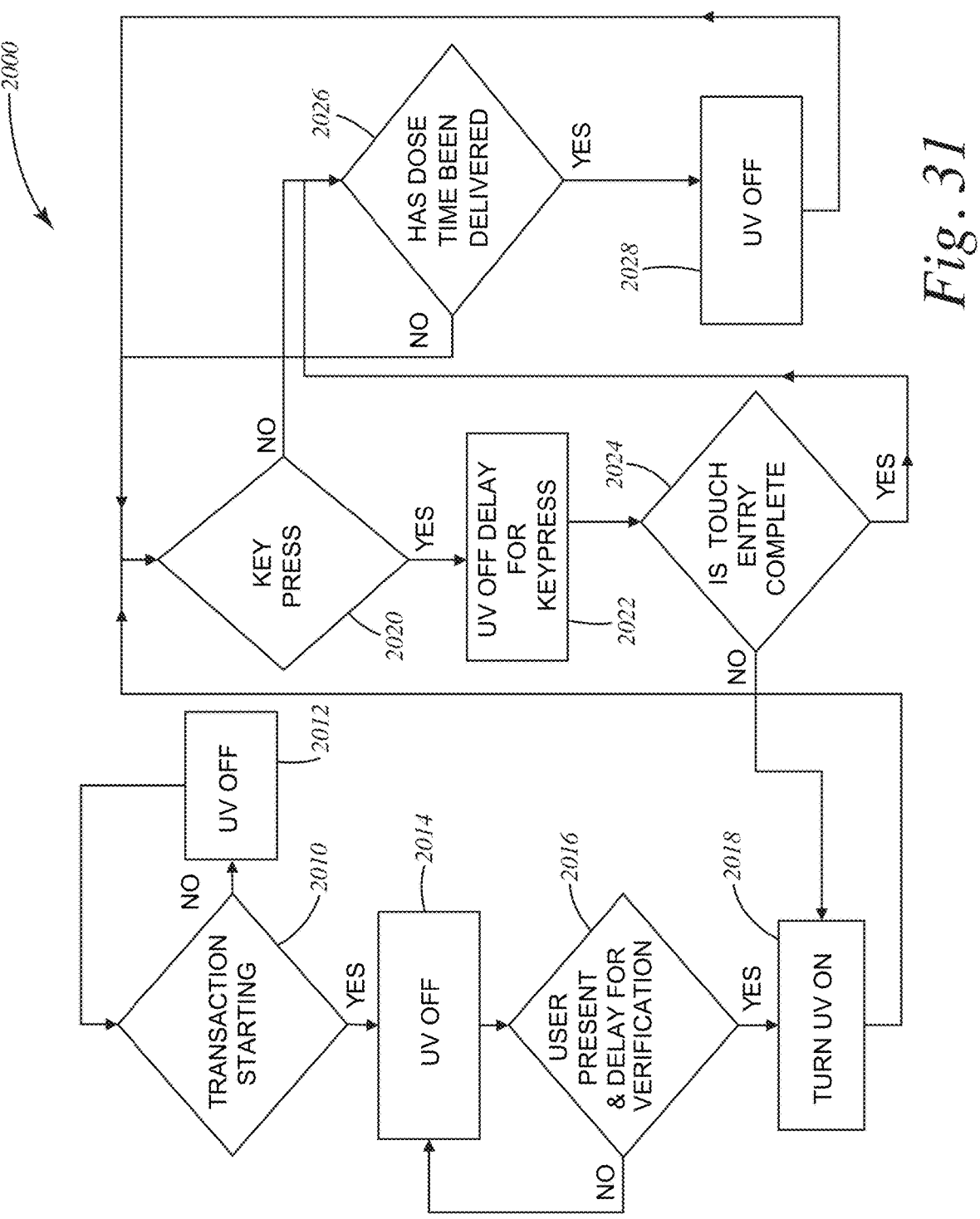
FIG. 31 shows a method of operation accordance with one embodiment.

A method of operation in accordance with one embodiment is shown in FIG. 31 and designated 2000. The method 2000 may pertain to presence detection and operation of the UV energy source 134 to disinfect the target area 10. The present disclosure is not limited to the method 2000—alternative methods of presence detection and operation may be implemented including the methods described in PCT Pub. 2015/184428, entitled UV GERMICIDAL DEVICES, SYSTEMS, AND METHODS, filed May 30, 2015, to Cole—the disclosure of which is hereby incorporated by reference in its entirety.

The method in accordance with one embodiment may discontinue a disinfecting process within 1 ms of detecting a user in proximity to the target surface 11 or touching the target surface 11.

The method in one embodiment may facilitate indicating multiple levels of disinfection. Varied levels may have efficacy against different pathogens. For instance, cold, flu, or COVID-19 may be more easily reduced while C-Diff may take longer. Feedback, such as a green LED, may be provided to identify initial reduction while still having a completed cycle or conducted a complete cycle for the more pathogens that involve longer disinfection times, depending on the application, such as a hospital or office building.

The method 2000 may enable continuous dosage delivery after touch entry starts. The system may start the dosage timer countdown once a touch starts. Instead of waiting, the system may immediately start dosing and stop only when touched. In one embodiment, the zonal control may be added to dose in areas the user is not touching. This control methodology may facilitate disinfection for fast-pace high usage kiosks (e.g., back to back customer kiosk entries), enabling customer to customer disinfection.

The method 2000 may include waiting for a transaction to start with the UV disinfection device in an off mode. Steps 2010, 2012, 2014. If a user's presence is detected 10, the method may involve waiting for verification pertaining to the user's presence. If the user's presence is verified, the UV disinfection's device may turn on to generate UV energy for disinfection. Steps 2016, 2018. In response to a touch or press of the target area 10, the method may involve turning off the UV energy source 134 to discontinue the supply of UV energy to the target area 10 in a delayed manner Steps 2020, 2022. If the touch or press of the target area 10 is incomplete, the UV energy source 134 may continue to supply UV energy to the target area 10. After the touch or press of the target area is complete, a determination of whether a dose time has been delivered may be conducted and the UV energy source may be discontinued. Steps 2024, 2026, 2028.

In the illustrated embodiment, if the UV energy source is on and a press or touch of the target area has not occurred, the method may determine whether a dose time has been delivered and the UV source may be discontinued in response to such a determination. Steps 2020, 2026, 2028.

Figure 32:
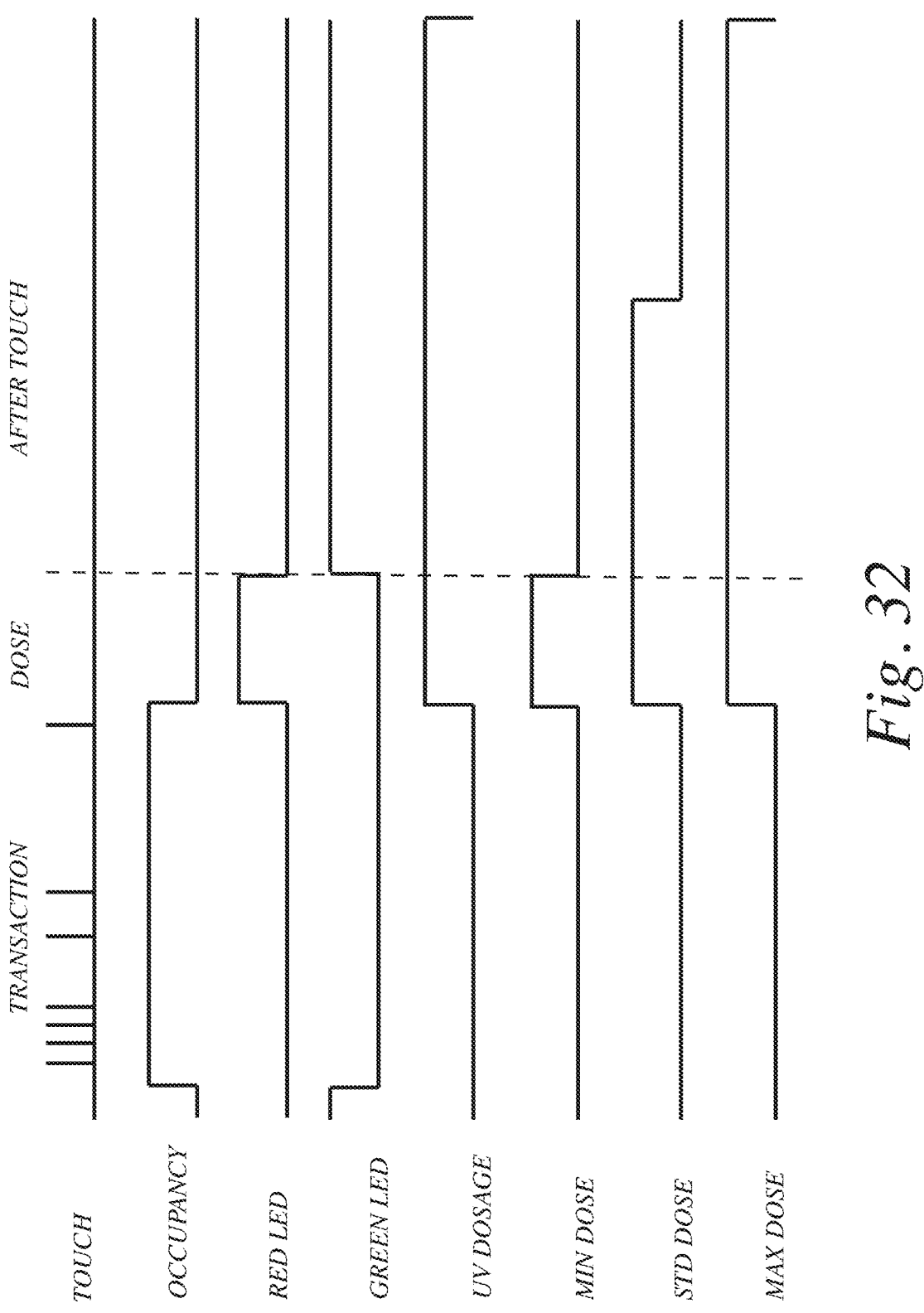
FIG. 32 shows a method of operation accordance with one embodiment.
Figure 33:
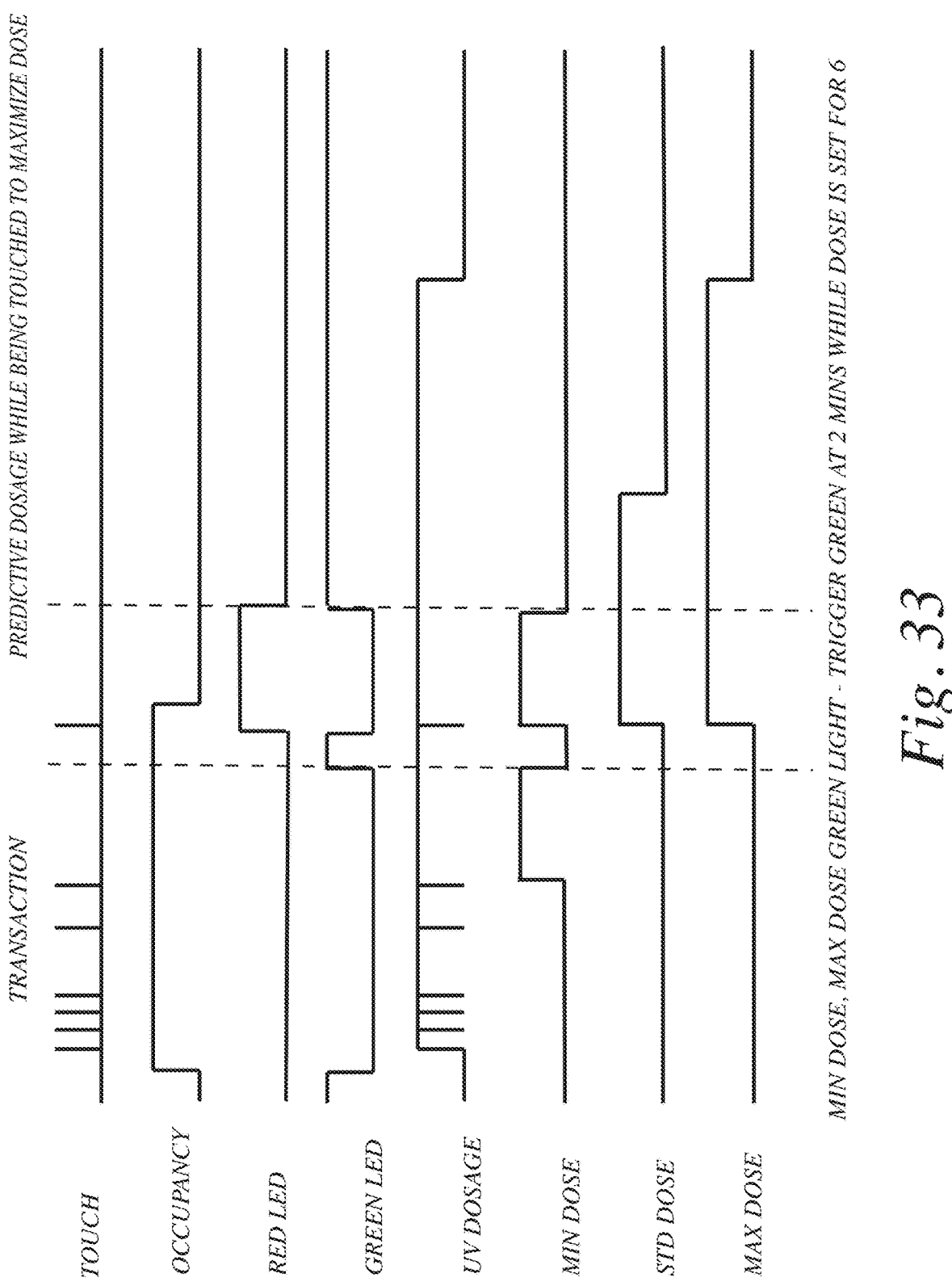
FIG. 33 shows a method of operation accordance with one embodiment.
Figure 34:
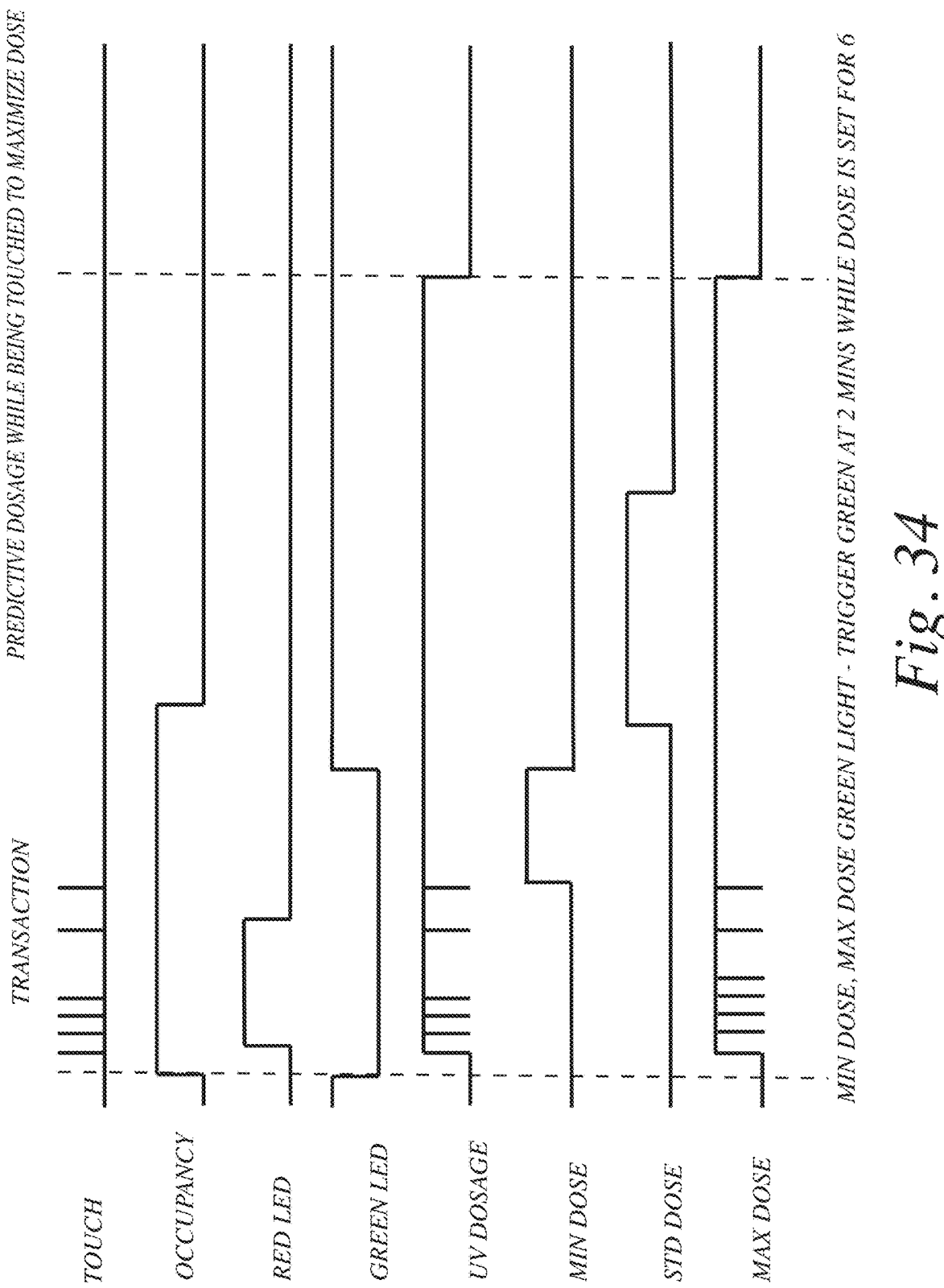
FIG. 34 shows a method of operation accordance with one embodiment.

Timing diagrams in accordance with several uses cases of the method 2000 are depicted in the illustrated embodiments of FIGS. 32-34. It is noted that the UV disinfection system 100 (e.g., a low profile disinfection system) may be used in many ways. In one embodiment, the use of fiber, as depicted in FIG. 29, may enable application of UV energy in a variety of applications. In one embodiment, the low profile nature of the UV disinfection system 100, as well as alternative embodiments of a UV disinfection system described herein, can be used on door plates, keyboards, touch surfaces, POS systems with minimal or reduced workflow impact toward maintaining or enhancing safety.

The method 2000 according to one embodiment is depicted in FIG. 32. After occupancy and touch is recognized, the system may wait to start dosage. After the user stops the UV dose starts, with the minimum dosage representing pathogens in group A or an easier to kill threshold. This may allow the user to see a green light for an indication of enhanced safety while the system is treating to the maximum dosage. This may produce higher confidence when back to back entries prevent a full dosage.

The method 2000 according to one embodiment is depicted in FIG. 33, showing the UV energy being distributed from the first touch but off when touched. A predictive touch algorithm may be configured to allow the dosing to potentially be complete while or shortly after entry. The one last touch restarts the timer and the min dosage feedback is enabled.

The method 2000 according to one embodiment is shown in FIG. 34, depicting a transition from short cycles like FIGS. 32 and 33 to a longer cycle where the max dosage threshold is enabled. The green LED (e.g., user feedback indicator) is enabled once min dosage is achieved.

The use cases in FIGS. 32-33 with respect to the method 2000 illustrate a binning aspect of the method 2000 for multiple types of disinfection criteria. For instance, in the illustrated embodiments, three dosage criteria are provided: 1) minimum dosage, 2) standard dosage, and 3) maximum dosage. These criteria relate to target dosage levels (minimum, standard, and maximum) for conditions specified for operating conditions of the UV disinfection system 100 and target pathogens. For instance, minimum dosage may correspond to a threshold dosage level above which a subset of target pathogens that are considered inactive, and the standard dosage may correspond to another threshold dosage level (potentially greater than the minimum dosage threshold) at which another subset of target pathogens are considered inactive. The maximum dosage may correspond to a threshold dosage level above which all of the target pathogens are considered inactive. As a result, in one embodiment, after the maximum dosage is attained, the UV disinfection system 100 may discontinue supplying UV dosage to the target surface.

In the illustrated embodiments of FIGS. 32-34, the timing signals associated with the minimum dosage, standard dosage, and maximum dosage show the duration over which a bin for each associated dosage is accumulated. An accumulator in accordance with one embodiment may correspond to a time accumulator or timer. For instance, in FIG. 32, the standard dosage signal begins accumulating in response to initiation of the UV dosage is initiated for the target surface, and ends in response to accumulation of UV dosage that is equal to or greater than the dosage threshold associated with the standard dosage criteria.

In one embodiment, the system may be configured to have a first and second dosage capability, where the first dose is considered sufficient when fast transactions are taking place and the second dosage is a preferred dosage when possible. Under these different conditions, the system may indicate the green LED while still intending on treating the surface longer. In one embodiment, the system may be configured to maximize that process until another touch occurs and then the system may start to process over again. It should also be noted that with such a low angle of UV exposure in one embodiment according to the present disclosure, the display may be treated while it is being touched and application of UV dosage may not be turned off at all until one or more or all of the dosage criteria are satisfied. This mode of operation may be dependent on the NIOSH requirements per person and may allow application of dosage while in use.

The start and complete criteria for each dosage criteria (e.g., minimum, standard, and maximum dosage) may vary. For instance, the minimum dosage accumulator may start accumulating according to one or more criteria different from the standard dosage accumulator or the maximum dosage criteria, or both. Likewise, the minimum dosage accumulator may be considered complete according to one or more criteria different from the standard dosage accumulator or the maximum dosage criteria, or both.

Additionally, or alternatively, one type of dosage accumulator may be reset according to one or more criteria different from another type of dosage accumulator. As an example, the standard dosage accumulator may be reset according to one or more criteria different from the minimum dosage criteria, such that the minimum dosage accumulator may continue to accumulate whereas the standard dosage accumulator may be reset in response to specific criteria being satisfied for the standard dosage criteria.

Zonal treatment may also be an option in accordance with one embodiment. Zonal treatment may involve treating another part of the display while in use but limiting exposure. One or more or all the various types of operational aspects (e.g. levers) may be used to treat the surface for enhanced or maximum reduction of pathogens.

In one embodiment, the target surface may be provided with an antimicrobial surface that interacts with UV for enhanced pathogen reduction, enabling time release antimicrobials.

In the method 2000 according the illustrated embodiments of FIGS. 33 and 34, UV dosage can be initiated near the beginning of a transaction (e.g., after the target surface is first touched as part of a transaction). This way, UV dosage may be supplied to the target surface throughout the transaction. For instance, UV dosage may be supplied over multiple touches associated with a user of the transaction. This way, UV dosage may be supplied to the target surface prior to the end of the transaction (which may be defined as the last touch associated with the transaction or as a period of time after the last touch associated with the transaction). If the amount of time between touches that are part of the transaction is greater than the amount time to satisfy one or more of the dosage criteria, the UV treatment system 100 may satisfy a disinfection criterion (e.g., minimum dosage achieved) before the end of the transaction—although the disinfection criterion may be reset in response to another touch of the target surface as part of the transaction.

By supplying UV dosage to the target surface throughout portions of the transaction, the overall amount of UV dosage per amount of time may be increased over an approach in which UV dosage is applied after the end of the transaction. For instance, in the illustrated embodiment of FIG. 33, the minimum dosage threshold is attained prior to the end of the transaction, and then reset in response to a touch that occurs as part of the transaction. The UV dosage may continue to be applied during the transaction, so that the dosage thresholds can be attained sooner after the end of the transaction than would otherwise occur if UV dosage were applied after the end of the transaction.

In the illustrated embodiments of FIGS. 32-34, the UV treatment system 100 may include an indicator system that identifies a disinfection status of the target surface. For instance, the indicator system may include a first LED (e.g., a green LED) that identifies whether the target surface is considered disinfected according to one or more of the disinfection criterion. In FIGS. 33-34, a green LED is enabled in response to the minimum dosage threshold being achieved, and reset in response to a touch that is considered to reset the dosage for achieving the minimum dosage threshold. The green LED may identify to the user that the target surface is considered disinfected according to one or more of the disinfection thresholds (e.g., the minimum dosage threshold). The indicator system may also include a second LED (e.g., a red LED) that indicates that target surface has been touched a threshold number of times or for a sufficient duration, or both, and that the UV dosage has not reached a target threshold identified for disinfection, such that the target surface may be considered to have a potential active pathogen present thereon.

In one embodiment, the UV dosage may be intermittently discontinued in response to a touch and then re-enabled after the touch ceases. As a result, the UV dosage may be applied earlier relative to a potential end of the transaction rather than waiting until an end of transaction timer expires after the last touch to initiate UV dosage.

In FIG. 32, the UV dosage is initiated a predetermined period of time after the last touch of a transaction occurs. As a result, the duration of time from the end of the transaction until the minimum, standard, and maximum dosage thresholds is greater than the duration of time identified in conjunction with the methods outlined in FIGS. 33 and 34.

In the illustrated embodiments of FIGS. 33 and 34, dosage amounts (e.g. duration of UV dosage) may be associated with multiple dosage criteria (e.g., minimum, standard, and maximum thresholds). The dosage amounts may be accumulated separately for each of the dosage criteria, such that separate dosage bins may be identified for each of the dosage criteria. By binning these sequences and dosage times, touches, interruptions, and totals, a controller or control system of the system may operate to optimize or enhance UV dosing of the system. The system may determine one or more operation parameters to achieve an ideal pathogen reduction period, and can adjust UV intensity according to combinational effects to enhance treatment of the target surface and to reduce pathogens.

IV. Control System

The UV disinfection device 100 in the illustrated embodiment may include a control system 150 operable to direct operation of the UV disinfection device 100 as described herein. For instance, the control system 150 may be configured to direct supply of power to the UV light source 134 to facilitate treatment of the target surface 11. As described herein, the control system 150 may be operably coupled to one or more sensors. The one or more sensors may be configured to sense a variety of information depending on the application. Example types of sensors include a passive infrared sensor (PIR sensor), a motion sensor, a contact center, a capacitive touch sensor, a USB input interface, an accelerometer, a temperature sensor, an RFID reader, a UV regulator sensor, and a motor sensor. It is noted that some of these examples include overlapping capabilities, such as the PIR sensor and the motion sensor, and in embodiments where such capabilities are described, one or more of such example sensors may be provided for such sensor capabilities.

The control system 150 in the illustrated embodiment may be operable to selectively control application of UV light from the UV energy source 134 to the target surface 11. The control system 150 may obtain information indicative of whether the device 10 is being used or whether a user is proximal to the device 10, and may control the UV energy source 134 based on this information.

The control system 150 may include any and all electrical circuitry and components to carry out the functions and algorithms described herein. Generally speaking, the control system 150 may include one or more microcontrollers, microprocessors, and/or other programmable electronics that are programmed to carry out the functions described herein. The control system 150 may additionally or alternatively include other electronic components that are programmed to carry out the functions described herein, or that support the microcontrollers, microprocessors, and/or other electronics. The other electronic components include, but are not limited to, one or more field programmable gate arrays, systems on a chip, volatile or nonvolatile memory, discrete circuitry, integrated circuits, application specific integrated circuits (ASICs) and/or other hardware, software, or firmware. Such components can be physically configured in any suitable manner, such as by mounting them to one or more circuit boards, or arranging them in other manners, whether combined into a single unit or distributed across multiple units. Such components may be physically distributed in different positions internal or external, or both, to the UV disinfection device 100, or they may reside in a common location within the UV disinfection device 100. When physically distributed, the components may communicate using any suitable serial or parallel communication protocol, such as, but not limited to, CAN, LIN, FireWire, I2C, RS-232, RS-485, and Universal Serial Bus (USB). In one embodiment, the control system local to a device (e.g., the UV disinfection device 100) may also interact with a cloud based control system, which may receive or transmit additional inputs obtained from external systems (e.g., other light fixtures or disinfection systems or environmental systems, or any combination thereof) to provide a greater view and understanding of the overall environment. The cloud based control system can also control a device directly based on additional protocols and information obtained from sensor data and other sources.

Figure 35:
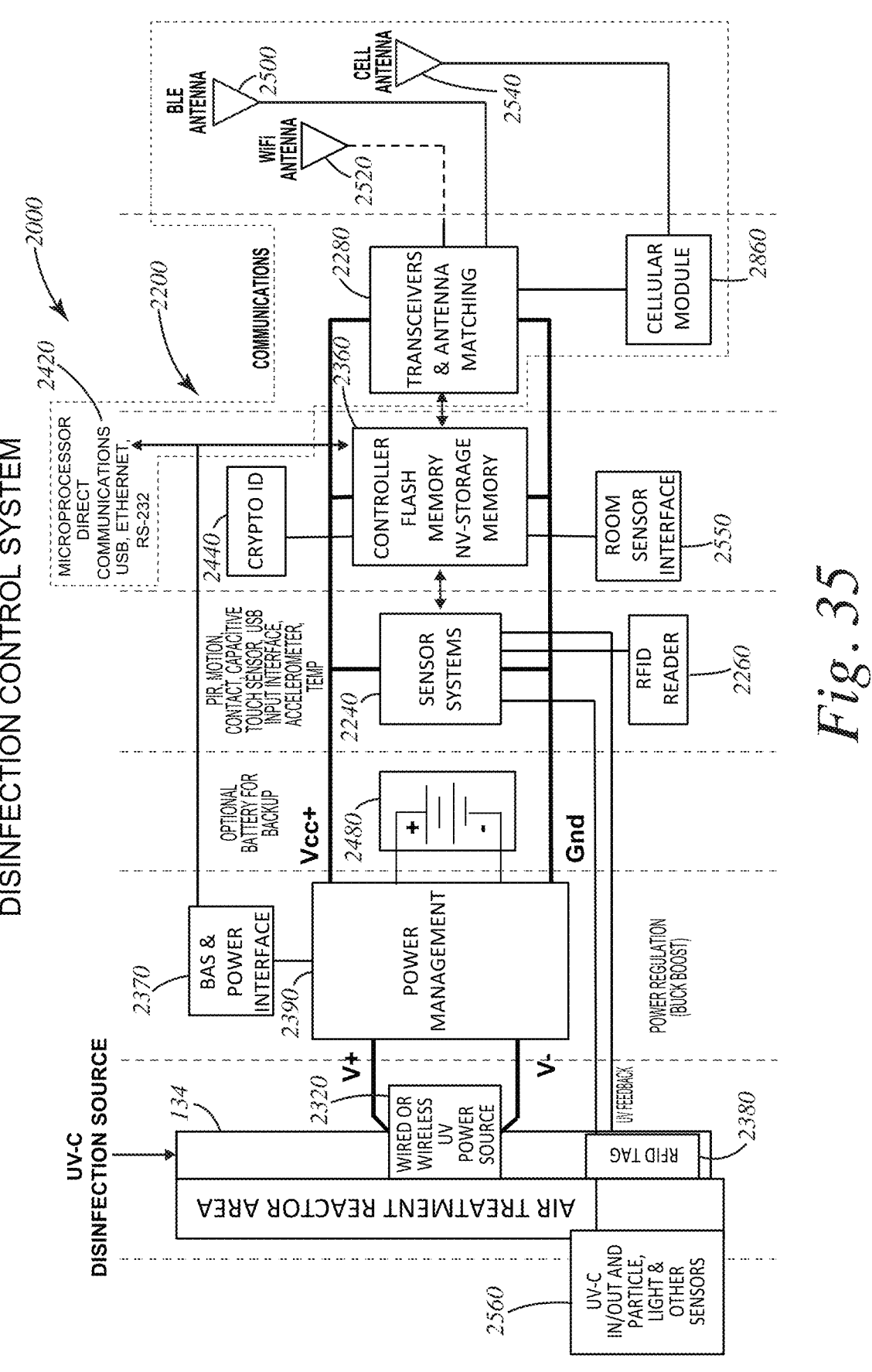
FIG. 35 shows a control system in accordance with one embodiment.

A control system 2000 for the UV disinfection device 100 in accordance with one embodiment is shown in FIG. 35. In one embodiment, the control system 2000 may be configured as an Internet-of Things ("IOT") hub or node within a network, as described herein. The control system 2000 in one embodiment may be provided in place of or to supplement the control system 150 described herein.

The control system 2000 may include power management capabilities and an optional battery management system for safety and emergency purposes. One or more sensors may be provided to detect presence and/or touch conditions for the device 10 or component for general data usage and analytics as well as helping to inform the systems control of events and conditions for response. The control system may include a UVC sensor to understand dose and time for the air reactor and the surface treatment. Power management may include one or more of the following operations: delayed off, intermittent cycle scheduling, dimming, power monitoring, and accounting, and on/off control.

The control system 2000 in the illustrated embodiment includes a UV energy power source 2320 (e.g., a UV-C power source) that enables UV intensity control and contact time control. The UV energy source 134 may be any UV source capable of generating UV energy at the target intensities, including UV-C light at the target intensities. The UV energy power source 2320 may be capable of controlling current and/or voltage supplied to the UV energy source 134, and may provide such power in a variety of ways. For instance, the UV energy power source 2320 may supply power directly via wires to the UV energy source 134, or the UV energy power source 2320 may supply power wirelessly to the UV energy source 134. In the wireless configuration, the UV energy power source 2320 may include a primary capable of transmitting power wirelessly, and the UV energy source 134 may include a secondary capable of receiving the wirelessly transmitted power.

The control system 2000 of this embodiment may include a controller 2360 capable of performing various functions pertaining to operation of the UV disinfection device 100. The controller can be a low current microprocessor configured on a regulated rail. The microprocessor can be configured to monitor temperature (e.g., ambient, source, and local microprocessor temperature), accelerometer values, voltage and current sensors, as well as any other suitable sensors for use in conjunction with a microprocessor, or any combination thereof. The microprocessor module can also allow for external communications and interface.

In the illustrated embodiment, the controller 2360 is coupled to a sensor system 2240 that provides the control system 2000 with various sensor inputs, such as PIR sensors, motion sensors, capacitive touch sensors, accelerometer and temperature sensors, and may provide an interface for RFID reader 2260. The data collected by these sensors may assist in controlling operation of the control system 2000 and in collecting data that may be relevant to tracking on infection-related events. The touch sensing aspect in accordance with one embodiment enables touch events to be used to trigger UV source activation, to interrupt disinfection cycles, and to provide valuable data in making dynamic adjustments to the UV parameters, such as cycle time and source intensity. The PIR sensor in one embodiment may enable heat and motion tracking. Additionally or alternatively, capacitive touch sensing may enable tracking touches of grab handles and non-switch surfaces.

In one embodiment, the control system 2000 may be coupled to a cloud system also as described herein as a cloud based control system. The cloud system may obtain multiple sensor readings for an environment, and direct operation of the UV disinfection device or one or more other devices, or a combination thereof, within a larger environment of multiple devices (e.g., multiple air pathogen reduction systems) in a connected pathogen reduction system.

The controller 2360 in one embodiment may monitor the current and voltage of power supplied to the UV energy source 134, and may determine whether the current and/or voltage are within preset ranges for proper operation and diagnostics. UV light energy 134 can present open circuits, short circuits, or impedance changes causing different operating voltages. The controller 2360 may identify such conditions based on the current and/or voltage and send information pertaining to such conditions to a remote network component, such as a network server on the cloud, as a service request. In one embodiment, the UV energy power source 2320 monitors the current and voltage to the UV energy source 134 and feeds that information back to the controller 2360. The controller 2360 may also include volatile and/or non-volatile storage memory. For example, the controller 2360 may include flash memory.

In one embodiment, the UV energy source 134 and control system 2000 have integrated RFID capabilities. An RFID tag 2380 disposed on the UV energy source 134 may allow the controller 2360 to uniquely identify the UV energy source 134 using an RFID reader 2260. This allows the control system 2000 to properly validate the UV energy source 134 and also allows new thresholds (e.g., operating currents and/or voltages and other operating parameters) to be transferred to the controller 2360 for the particular UV energy source 134 connected to the UV disinfection device 100. These thresholds may change by manufacturer or lamp time and can also be changed over time as the controller 2360 adapts and learns the operating parameters of the UV energy source 134.

The UV energy power source 2320 in one embodiment includes an amplifier circuit, where an amplifier gain can be changed to increase or decrease intensity of the UV light source 134. The amplifier may change the voltage applied to the UV light power source 2320 to within allowed thresholds. It is noted that higher thresholds or operating near the upper end of a voltage range of the UV light source 134 may adversely affect the life of the UV light source 134. The operating intensity thresholds, operating ranges, or other operating conditions for the UV light source 134 may also be pushed and saved to the RFID tag 238. For instance, the hours at each intensity level may be helpful to the controller 2360 as it may accumulate the time at each intensity for the UV light source 134 to enable total end-of-life calculations. This information may be persistent to the RFID tag 2380 of the UV light source 134.

A communication interface 2200 of the control system 2000 may be provided to receive information from and transmit information to external electronic devices. For instance, the communication interface 2200 may include a USB interface 2420 (or other wired communication interface, such as Ethernet or RS-232) or a BTLE interface (or other wireless communication interface) that can be configured to allow external electronic devices, such as a smartphone, tablet computer, or other mobile electronic device to automatically write UV parameters and other relevant values into the control system 2000.

In some applications, additional security-related components may be provided in the control system 2000. For example, a crypto chip may be included to provide each unit with a unique ID. Other mechanisms for identifying each UV disinfection device 100 may be provided. The security may also be augmented with a token and SSID for security purposes stored in non-volatile memory set up by installation staff through BTLE or USB program for WiFi interface. This crypto chip may be provided for an additional security measure and may be configured to create a disinfection and room occupation tracking device that can have the security conditions considered sufficient to write directly into an electronic medical record.

In one embodiment, the communication interface 2200 of the control system 2000 has BTLE and/or Mesh capabilities. The mesh network can be Zigbee or BACNet to meet specific regulatory requirements or hospital specifications. In one embodiment, a cellular module 2860 may be used to communicate the data to an external device (e.g., the cloud) as an alternative source of information gathering. As shown, the control system 2000 may include transceivers and antenna matching circuitry 2280 and a cellular module 2860 that are coupled to corresponding antennas 2520, 2500, 2540. The controller 2360 may also have ports to allow direct wired connections, for example, using USB, Ethernet, and RS-232 protocols.

In some applications, the control system 2000 may have the ability to operate on battery power. The battery version may be provided with a battery 2480, which may be the power source for the UV disinfection device 100. The battery-based system may be chargeable in a variety of ways, including wired and wireless charging configurations. The power storage may be sized for UV dose and interval, and may be connected to charging equipment or directly chargeable. It may also have various indicators for providing feedback to a user.

As noted above, the UV light source 134 (e.g., UV-C lamp) may have an RFID tag 2380 and the control system 2000 may have an RFID reader 2260 to understand when the UV light source 134 has reached end-of-life to encourage appropriate use and maintenance. UV light sources 134 often have a life based on a number of hours as they self-destruct due to the nature of UV light, including UV-C light. The control system 2000, for example, through the controller 2360, may keep track of lamp "on time" by reading from and writing to memory resident on the RFID tag 2380. The control system 2000 may adjust the actual "on time" by a correlation factor to compensate for lamp intensity. For example, the control system 2000 may increment the lamp life counter by less than the actual "on time" for operation that occurs when the lamp intensity is reduced and may increase the lamp life counter by more than the actual "on time" for operation when the lamp intensity is increased. The correlation factor (or intensity adjustment factor) may be provided by the lamp manufacturing, may be determined through tests of the UV light source 160, or may be estimated based on past experience.

The communication interface 2200 of the control system 2000 may also have USB and Power over Ethernet ("POE") circuitry 2370, which may enable usage without additional power cord requirements for this equipment. In one embodiment, the power management circuitry 2390 may allow inputs from power generating sources and various voltages enabling flexible power adaptation. For instance, the power management circuitry 2390 may allow AC power to pass through so that the host piece of equipment is undisturbed. When the UV disinfection device 100 is integrated into another electronic device, the power management circuitry 2390 may allow the UV disinfection device 100 to draw power from the power supply for the host electronic device as the power source. A single outlet can be used to avoid potential confusion when plugging in the device. The power management circuitry 2390 may be operable to power from a variety of sources, including wireless, USB, DC, and battery sources. In one embodiment the power regulation is done in a buck boost manner to provide an energy harvesting power supply that produces a regulated power source when voltage is produced by various power sources.

UV light regulator sensor circuitry 2560 may be operable to provide feedback indicative of an intensity of UV-C light being directed into the room area 50.

In one embodiment, as discussed herein, the control system 200 may include a sensor interface 2550 operably coupled to the controller 2360. The sensor interface 2550 may be configured to provide feedback indicative of whether the target surface 11 is being used or touched or whether a person is proximal to the target surface 11, or a combination thereof.

In the illustrated embodiment, the control system 2000 may use feedback from the sensor interface 2550 to determine whether to direct UV light toward the target surface 11, or to discontinue providing UV light toward the target surface 11.

It is to be understood that the room sensor interface 2550 may be separate from the control system 2000 in an external device capable of communicating information. For instance, the sensor interface 2550 may be a motion sensor (e.g., a PIR sensor) capable of sensing the presence of one or more persons proximal to the target surface 11. This motion sensor may communicate wirelessly with the control system 2000 or with an intermediary device capable of relaying occupancy information to the control system 2000.

In the drawings, Roman numerals such as "II", "VII", "VIII", "IX", "XV", "XVI", and "XVII" are used to indicate sectional, detailed, or cutaway views corresponding to specific figure numbers. These numerals identify section lines or areas in certain figures from which subsequent figures are derived. For example, the numerals "VII" and "VIII" in FIG. 5 correspond to sectional views that are illustrated in FIGS. 7 and 8, respectively.

The above description is that of current embodiments of the invention. Various alterations and changes can be made without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular.

The invention claimed is:

1. A UV disinfection device for a display having a target surface defining a region of intended human interaction with the display, the device comprising:
   a support member operable to facilitate mounting the UV disinfection device proximate to a proximal edge of the target surface of the display, wherein the target surface further comprises a distal edge spaced apart from the UV disinfection device and opposite the proximal edge;
   a germicidal energy source operable to generate UV energy, wherein the germicidal energy source is a UV light emitting diode (LED);
   a UV reflection chamber having a first reflector and an exit interface through which UV energy exits the UV reflection chamber, the first reflector operable to receive UV energy generated by the germicidal energy source and to direct UV energy toward the exit interface;
   the first reflector operable to direct UV energy the target surface through the exit interface; and
   the exit interface having a proximal portion proximate the proximal edge of the target surface and a distal portion distal from to the proximal edge of the target surface, the exit interface having an exit interface height defined between the proximal portion and the distal portion and an exit interface length defined along a direction transverse to the exit interface height, wherein the exit interface height is significantly less than a target surface distance between the proximal edge of the target surface and the distal edge of the target surface;
   an elongated UV diffuser separate from the UV LED and having an elongated dimension corresponding to the exit interface length, the elongated UV diffuser disposed adjacent to and optically coupled with the UV LED within the UV reflection chamber and wherein the UV LED is arranged to transmit UV energy into the elongated UV diffuser and the elongated UV diffuser is arranged to receive UV energy output from the UV LED;
   wherein the UV LED, the elongated UV diffuser, and the UV reflection chamber cooperate to facilitate spreading UV energy within the UV reflection chamber and provide an elongated emission pattern of UV energy extending in the direction of the exit interface length;
   wherein the UV reflection chamber is configured to reflect UV energy within the UV reflection chamber until the UV energy is directed through the exit interface at an exit angle of incidence sufficient to permit passage of the UV energy directly toward the distal edge of the target surface; and
   wherein the UV reflection chamber is configured to direct a greater amount of UV energy through the distal portion of the exit interface than through the proximal portion of the exit interface to compensate for inverse square losses over the target surface distance between the proximal edge of the target surface and the distal edge of the target surface.

2. The UV disinfection device of claim 1 wherein:
   the distal portion and the proximal portion define an exit interface plane through which UV energy traverses toward the target surface; and
   the UV energy exits the exit interface between the proximal portion and the distal portion of the exit interface.

3. The UV disinfection device of claim 1 wherein the exit interface height corresponds to a distance between the proximal portion and the distal portion.

4. The UV disinfection device of claim 1 wherein a distance between the distal portion and the proximal portion is 2 mm or less.

5. The UV disinfection device of claim 1 wherein an angle between the exit interface and the target surface is less than 90°.

6. The UV disinfection device of claim 1 wherein the UV energy reflected from the first reflector is directed toward the target surface at an angle less than 90° relative to the exit interface.

7. The UV disinfection device of claim 1 wherein a ratio of the target surface distance to the exit interface height is greater than 5.

8. The UV disinfection device of claim 7 wherein the ratio is greater than 100.

9. The UV disinfection device of claim 1 wherein the UV energy output from the exit interface is substantially confined to a UV energy region, where a distance between a boundary of the UV energy region and the target surface is significantly less than the target surface distance.

10. The UV disinfection device of claim 1 wherein the exit interface includes a mask operable to affect a distribution of UV energy output from the exit interface.

11. The UV disinfection device of claim 1 wherein the exit interface includes a composite lens operable to output a UV light pattern to a target distance and dosage with a generally uniform distribution at the target surface after accounting for the inverse square losses.

12. The UV disinfection device of claim 1 wherein the UV energy output from the exit interface is substantially confined to a UV energy region, wherein the UV energy region is defined by the target surface and an opposing boundary line that converges with the target surface.

13. The UV disinfection device of claim 1 wherein the elongated UV diffuser is in the shape of a rod.

14. The UV disinfection device of claim 13 wherein a gel is provided in contact with the elongated UV diffuser and the germicidal energy source, wherein the gel optically couples the germicidal energy source to the elongated UV diffuser.

15. A UV disinfection device for disinfecting a target surface associated with a display, the target surface defining a region of intended human interaction with the display, the UV disinfection device comprising:

a support member operable to facilitate mounting the UV disinfection device proximate to a proximal edge of the target surface of the display, wherein the target surface further comprises a distal edge spaced apart from the UV disinfection device and opposite the proximal edge;

a germicidal energy source operable to generate UV energy, wherein the germicidal energy source is a UV light emitting diode (LED);

a UV reflection chamber having a first reflector and an exit interface through which UV energy exits the UV reflection chamber, the first reflector operable to receive UV energy generated by the germicidal energy source and to direct UV energy toward the exit interface;

the exit interface being adjacent the proximal edge of the target surface, the exit interface having a proximal portion proximate the proximal edge of the target surface and a distal portion distal from to the proximal edge of the target surface, the exit interface having an exit interface height significantly less than a target surface distance between the proximal edge of the target surface and the distal edge of the target surface, the exit interface having an exit interface length defined along a direction transverse to the exit interface height;

the first reflector configured to direct the UV energy through the exit interface and to the target surface; and an elongated UV diffuser separate from the UV LED and having an elongated dimension corresponding to the exit interface length, the elongated UV diffuser disposed adjacent to and optically coupled with the UV LED within the UV reflection chamber and wherein the UV LED is arranged to transmit UV energy into the elongated UV diffuser and the elongated UV diffuser is arranged to receive UV energy output from the UV LED;

wherein the UV LED, the elongated UV diffuser, and the UV reflection chamber cooperate to facilitate spreading UV energy within the UV reflection chamber and provide an elongated emission pattern of UV energy along the exit interface length;

wherein the UV reflection chamber is configured to reflect UV energy within the UV reflection chamber until the UV energy is directed through the exit interface at an exit angle of incidence sufficient to permit passage of the UV energy directly toward the distal edge of the target surface; and wherein the UV energy output from the exit interface is substantially confined to a UV energy region, the UV energy region being defined by the target surface and a boundary plane that converges toward the target surface, wherein the boundary plane intersects the distal portion of the exit interface and is defined by the exit angle of incidence; and wherein the UV reflection chamber is configured to direct a greater amount of UV energy through the distal portion of the exit interface than through the proximal portion of the exit interface to compensate for the inverse square losses over the target surface distance between the proximal edge of the target surface and the distal edge of the target surface.

16. The UV disinfection device of claim 15 wherein the boundary plane converges with the target surface at a point distal from the exit interface.

17. The UV disinfection device of claim 15 wherein the exit interface height is 2 mm or less.

18. The UV disinfection device of claim 15 wherein an angle between the exit interface and the target surface is less than 90°.

19. The UV disinfection device of claim 15 wherein the UV energy reflected from the first reflector is directed toward the target surface at an angle less than 90° relative to the exit interface.

20. The UV disinfection device of claim 15 wherein a ratio of the target surface distance to the exit interface height is greater than 5.

21. The UV disinfection device of claim 20 wherein the ratio is greater than 100.

22. The UV disinfection device of claim 15 wherein a distance between the boundary plane of the UV energy region and the target surface is significantly less than the target surface distance.

23. The UV disinfection device of claim 15 wherein the exit interface includes a mask operable to affect a distribution of UV energy output from the exit interface.

24. The UV disinfection device of claim 15 wherein the exit interface includes a composite lens operable to output a UV light pattern to a target distance and dosage with a generally uniform distribution at the target surface after accounting for the inverse square losses.

25. The UV disinfection device of claim 15 wherein the elongated UV diffuser is rod-shaped.

26. The UV disinfection device of claim 25 wherein a gel is provided in contact with the elongated UV diffuser and the germicidal energy source, wherein the gel optically couples the germicidal energy source to the elongated UV diffuser.

27. The UV disinfection device of claim 1 wherein the first reflector is positioned in opposition to the exit interface, wherein the distal portion and the proximal portion define an exit interface plane through which UV energy traverses toward the target surface, wherein UV energy reflected from the first reflector is directed toward the target surface at an angle less than 90° relative to the exit interface plane.

28. The UV disinfection device of claim 1 wherein the UV energy output from the exit interface is substantially confined to a UV energy region, the UV energy region being defined by the target surface and a boundary plane that converges toward the target surface, wherein the boundary plane intersects the distal portion of the exit interface and is defined by the exit angle of incidence.

29. The UV disinfection device of claim 28 wherein a ratio of the target surface distance to the exit interface height is greater than 5, and wherein the exit angle of incidence is greater than 0° and less than 5°.

30. The UV disinfection device of claim 15 wherein the first reflector is positioned in opposition to the exit interface, wherein the distal portion and the proximal portion define an exit interface plane through which UV energy traverses toward the target surface, wherein UV energy reflected from the first reflector is directed toward the target surface at an angle less than 90° relative to the exit interface plane.

31. The UV disinfection device of claim 15 wherein a ratio of the target surface distance to the exit interface height is greater than 5, and wherein the exit angle of incidence is greater than 0° and less than 5°.

* * * * *